(12) United States Patent
Richardson et al.

(10) Patent No.: US 7,854,761 B2
(45) Date of Patent: Dec. 21, 2010

(54) METHODS FOR VENOUS VALVE REPLACEMENT WITH A CATHETER

(75) Inventors: Leonard B. Richardson, Minneapolis, MN (US); Jason P. Hill, Cottage Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1907 days.

(21) Appl. No.: 10/741,995

(22) Filed: Dec. 19, 2003

(65) Prior Publication Data

US 2005/0137676 A1    Jun. 23, 2005

(51) Int. Cl.
*A61F 2/24* (2006.01)
(52) U.S. Cl. ............... 623/2.11; 623/910; 623/1.24
(58) Field of Classification Search .......... 623/1.2, 623/1.22, 1.16, 1.27, 1.24, 1.26, 2.11–2.19, 623/902–904, 909, 910; 606/194, 195
See application file for complete search history.

(56) References Cited

U.S. PATENT DOCUMENTS

| | | | |
|---|---|---|---|
| 4,994,077 A | 2/1991 | Dobben | 623/2 |
| 5,358,518 A | 10/1994 | Camilli | 623/2 |
| 5,411,552 A | 5/1995 | Andersen et al. | 623/2 |
| 5,500,014 A | 3/1996 | Quijano et al. | 623/2 |
| 6,092,529 A | 7/2000 | Cox | 128/898 |
| 6,200,336 B1 | 3/2001 | Pavenik et al. | 623/1.15 |
| 6,287,334 B1 | 9/2001 | Moll et al. | 623/1.24 |
| 6,299,637 B1 | 10/2001 | Shaolian et al. | 623/1.24 |
| 6,315,793 B1 | 11/2001 | Bokros et al. | 623/1.24 |
| 6,440,164 B1 | 8/2002 | DiMatteo et al. | 623/1.24 |
| 6,494,909 B2 | 12/2002 | Greenhalgh | 623/1.24 |
| 6,503,272 B2 | 1/2003 | Duerig et al. | 623/1.24 |
| 6,527,800 B1 | 3/2003 | McGuckin, Jr. et al. | 623/1.24 |
| 6,562,069 B2 | 5/2003 | Cai et al. | 623/2.12 |
| 6,585,761 B2 | 7/2003 | Taheri | 623/1.24 |
| 6,602,286 B1 | 8/2003 | Strecker | 623/1.24 |
| 6,605,112 B1 | 8/2003 | Moll et al. | 623/1.24 |
| 6,632,243 B1 | 10/2003 | Zadno-Azizi et al. | 623/1.24 |

(Continued)

FOREIGN PATENT DOCUMENTS

EP    0667133    8/1995

(Continued)

OTHER PUBLICATIONS

US 6,673,110, 01/2004, Alfieri et al. (withdrawn)

(Continued)

*Primary Examiner*—Brian E. Pellegrino
(74) *Attorney, Agent, or Firm*—Brooks, Cameron & Huebsch, PLLC

(57) ABSTRACT

A venous valve apparatus, system and method for valve replacement. The valve includes a valve frame, a valve leaflet joined to the valve frame, and a support frame. The valve leaflet includes surfaces defining a reversibly sealable opening for unidirectional flow of a liquid. The support frame meets the valve frame on an axis, where the valve frame and the support frame extend from the axis in an opposing direction. The system further includes a catheter, where the valve can be reversibly joined to the catheter at a location between a proximal end and a distal end of the catheter. The system can be used to deploy the valve from the catheter at a predetermined location.

17 Claims, 9 Drawing Sheets

U.S. PATENT DOCUMENTS

| | | | |
|---|---|---|---|
| 6,666,885 B2 | 12/2003 | Moe | 623/2.12 |
| 6,666,886 B1 | 12/2003 | Tranquillo et al. | 623/2.42 |
| 6,669,725 B2 | 12/2003 | Scott | 623/2.36 |
| 6,673,109 B2 | 1/2004 | Cox | 623/2.12 |
| 6,676,698 B2 | 1/2004 | McGuckin, Jr. et al. | 623/1.24 |
| 6,676,702 B2 | 1/2004 | Mathis | 623/2.36 |
| 6,682,558 B2 | 1/2004 | Tu et al. | 623/2.11 |
| 6,682,559 B2 | 1/2004 | Myers et al. | 623/2.13 |
| 6,685,739 B2 | 2/2004 | DiMatteo et al. | 623/1.24 |
| 6,692,512 B2 | 2/2004 | Jang | 606/200 |
| 6,695,866 B1 | 2/2004 | Kuehn et al. | 606/213 |
| 6,695,878 B2 | 2/2004 | McGuckin, Jr. et al. | 623/1.19 |
| 6,709,456 B2 | 3/2004 | Langberg et al. | 623/2.37 |
| 6,709,457 B1 | 3/2004 | Otte et al. | 623/2.4 |
| 6,716,241 B2 | 4/2004 | Wilder et al. | 623/1.24 |
| 6,716,244 B2 | 4/2004 | Klaco | 623/2.4 |
| 6,719,767 B1 | 4/2004 | Kimblad | 606/151 |
| 6,719,784 B2 | 4/2004 | Henderson | 623/1.44 |
| 6,719,786 B2 | 4/2004 | Ryan et al. | 623/2.11 |
| 6,719,787 B2 | 4/2004 | Cox | 623/2.12 |
| 6,719,788 B2 | 4/2004 | Cox | 623/2.12 |
| 6,719,789 B2 | 4/2004 | Cox | 623/2.13 |
| 6,719,790 B2 | 4/2004 | Brendzel et al. | 623/2.4 |
| 6,723,038 B1 | 4/2004 | Schroeder et al. | 600/16 |
| 6,723,122 B2 | 4/2004 | Yang et al. | 623/2.1 |
| 6,723,123 B1 | 4/2004 | Kazatchkov et al. | 623/2.2 |
| 6,726,715 B2 | 4/2004 | Sutherland | 623/2.1 |
| 6,726,716 B2 | 4/2004 | Marquez | 623/2.36 |
| 6,726,717 B2 | 4/2004 | Alfieri et al. | 623/2.36 |
| 6,730,118 B2 | 5/2004 | Spenser et al. | 623/1.24 |
| 6,730,121 B2 | 5/2004 | Ortiz et al. | 623/2.17 |
| 6,730,122 B1 | 5/2004 | Pan et al. | 623/2.33 |
| 6,736,845 B2 | 5/2004 | Marquez et al. | 623/2.11 |
| 6,736,846 B2 | 5/2004 | Cox | 623/2.12 |
| 6,749,630 B2 | 6/2004 | McCarthy et al. | 623/2.36 |
| 6,752,813 B2 | 6/2004 | Goldfarb et al. | 606/139 |
| 6,752,828 B2 | 6/2004 | Thornton | 623/1.24 |
| 6,755,857 B2 | 6/2004 | Peterson et al. | 623/2.17 |
| 6,761,734 B2 | 7/2004 | Suhr | 623/1.35 |
| 6,761,735 B2 | 7/2004 | Eberhardt et al. | 623/2.1 |
| 6,764,494 B2 | 7/2004 | Menz et al. | 606/159 |
| 6,764,508 B1 | 7/2004 | Roehe et al. | 623/2.11 |
| 6,764,509 B2 | 7/2004 | Chinn et al. | 623/2.12 |
| 6,764,510 B2 | 7/2004 | Vidlund et al. | 623/2.34 |
| 6,767,362 B2 | 7/2004 | Schreck | 623/2.11 |
| 6,769,434 B2 | 8/2004 | Liddicoat et al. | 128/898 |
| 6,770,083 B2 | 8/2004 | Seguin | 606/142 |
| 6,780,200 B2 | 8/2004 | Jansen | 623/2.17 |
| 6,786,924 B2 | 9/2004 | Ryan et al. | 623/2.36 |
| 6,786,925 B1 | 9/2004 | Schoon et al. | 623/2.38 |
| 6,790,229 B1 | 9/2004 | Berreklouw | 623/2.1 |
| 6,790,230 B2 | 9/2004 | Beyersdorf et al. | 623/2.18 |
| 6,790,231 B2 | 9/2004 | Liddicoat et al. | 623/2.37 |
| 6,793,673 B2 | 9/2004 | Kowalsky et al. | 623/2.36 |
| 6,797,000 B2 | 9/2004 | Simpson et al. | 623/2.15 |
| 6,797,001 B2 | 9/2004 | Mathis et al. | 623/2.37 |
| 6,797,002 B2 | 9/2004 | Spence et al. | 623/2.38 |
| 6,802,860 B2 | 10/2004 | Cosgrove et al. | 623/2.11 |
| 6,805,710 B2 | 10/2004 | Bolling et al. | 623/2.36 |
| 6,805,711 B2 | 10/2004 | Quijano et al. | 623/2.37 |
| 6,810,882 B2 | 11/2004 | Langberg et al. | 128/898 |
| 6,821,297 B2 | 11/2004 | Snyders | 623/2.18 |
| 6,824,562 B2 | 11/2004 | Mathis et al. | 623/2.36 |
| 6,830,584 B1 | 12/2004 | Seguin | 623/2.11 |
| 6,830,585 B1 | 12/2004 | Artof et al. | 623/2.11 |
| 6,837,902 B2 | 1/2005 | Nguyen et al. | 623/2.13 |
| 6,840,246 B2 | 1/2005 | Downing | 128/898 |
| 6,840,957 B2 | 1/2005 | DiMatteo et al. | 623/1.24 |
| 6,846,324 B2 | 1/2005 | Stobie | 623/2.11 |
| 6,846,325 B2 | 1/2005 | Liddicoat | 623/2.4 |
| 6,858,039 B2 | 2/2005 | McCarthy | 623/2.36 |
| 6,869,444 B2 | 3/2005 | Gabbay | 623/2.36 |
| 6,872,226 B2 | 3/2005 | Cali et al. | 623/2.13 |
| 6,875,224 B2 | 4/2005 | Grimes | 606/219 |
| 6,875,230 B1 | 4/2005 | Morita et al. | 623/2.12 |
| 6,875,231 B2 | 4/2005 | Anduiza et al. | 623/2.14 |
| 6,881,199 B2 | 4/2005 | Wilk et al. | 604/9 |
| 6,881,224 B2 | 4/2005 | Kruse et al. | 623/2.11 |
| 6,883,522 B2 | 4/2005 | Spence et al. | 128/898 |
| 6,890,352 B1 | 5/2005 | Lentell | 623/2.27 |
| 6,890,353 B2 | 5/2005 | Cohn et al. | 623/2.37 |
| 6,893,459 B1 | 5/2005 | Macoviak | 623/2.11 |
| 6,893,460 B2 | 5/2005 | Spenser et al. | 623/2.14 |
| 6,896,700 B2 | 5/2005 | Lu et al. | 623/2.34 |
| 6,902,576 B2 | 6/2005 | Drasler et al. | 623/1.24 |
| 6,908,478 B2 | 6/2005 | Alferness et al. | 623/1.11 |
| 6,908,481 B2 | 6/2005 | Cribier | 623/2.11 |
| 6,911,043 B2 | 6/2005 | Myers et al. | 623/2.13 |
| 6,913,608 B2 | 7/2005 | Liddicoat et al. | 606/151 |
| 6,916,338 B2 | 7/2005 | Speziali | 623/2.12 |
| 6,918,917 B1 | 7/2005 | Nguyen et al. | 606/139 |
| 6,921,407 B2 | 7/2005 | Nguyen et al. | 606/142 |
| 6,921,811 B2 | 7/2005 | Zamora et al. | 536/21 |
| 6,926,715 B1 | 8/2005 | Hauck et al. | 606/41 |
| 6,926,730 B1 | 8/2005 | Nguyen et al. | 606/213 |
| 6,929,653 B2 | 8/2005 | Strecter | 606/200 |
| 6,932,838 B2 | 8/2005 | Schwartz et al. | 623/1.23 |
| 6,936,067 B2 | 8/2005 | Buchanan | 623/2.28 |
| 6,939,359 B2 | 9/2005 | Tu et al. | 606/159 |
| 6,942,694 B2 | 9/2005 | Liddicoat et al. | 623/2.36 |
| 6,945,957 B2 | 9/2005 | Freyman | 604/96.01 |
| 6,945,978 B1 | 9/2005 | Hyde | 606/142 |
| 6,945,996 B2 | 9/2005 | Sedransk | 623/2.12 |
| 6,945,997 B2 | 9/2005 | Huynh et al. | 623/2.17 |
| 6,949,122 B2 | 9/2005 | Adams et al. | 623/2.36 |
| 6,951,571 B1 | 10/2005 | Srivastava | 623/1.24 |
| 6,951,573 B1 | 10/2005 | Dilling | 623/2.2 |
| 6,953,332 B1 | 10/2005 | Kurk et al. | 425/275 |
| 6,955,689 B2 | 10/2005 | Ryan et al. | 623/2.36 |
| 6,958,076 B2 | 10/2005 | Acosta et al. | 623/1.24 |
| 6,962,605 B2 | 11/2005 | Cosgrove et al. | 623/2.36 |
| 6,964,682 B2 | 11/2005 | Nguyen-Thien-Nhon et al. | 623/2.11 |
| 6,964,683 B2 | 11/2005 | Kowalsky et al. | 623/2.36 |
| 6,964,684 B2 | 11/2005 | Ortiz et al. | 623/2.37 |
| 6,966,925 B2 | 11/2005 | Stobie | 623/2.11 |
| 6,966,926 B2 | 11/2005 | Mathis | 623/2.36 |
| 6,974,464 B2 | 12/2005 | Quijano et al. | 606/108 |
| 6,974,474 B2 | 12/2005 | Pavcnik et al. | 623/1.24 |
| 6,974,476 B2 | 12/2005 | McGuckin, Jr. et al. | 623/2.36 |
| 6,976,995 B2 | 12/2005 | Mathis et al. | 623/2.37 |
| 6,979,350 B2 | 12/2005 | Moll et al. | 623/1.24 |
| 6,986,775 B2 | 1/2006 | Morales et al. | 606/139 |
| 6,989,027 B2 | 1/2006 | Allen et al. | 623/2.18 |
| 6,989,028 B2 | 1/2006 | Lashinski et al. | 623/2.37 |
| 6,997,950 B2 | 2/2006 | Chawla | 623/2.1 |
| 6,997,951 B2 | 2/2006 | Solem et al. | 623/2.37 |
| 7,004,176 B2 | 2/2006 | Lau | 128/898 |
| 7,007,396 B2 | 3/2006 | Rudko et al. | 33/512 |
| 7,011,669 B2 | 3/2006 | Kimblad | 606/151 |
| 7,011,681 B2 | 3/2006 | Vesely | 623/2.11 |
| 7,011,682 B2 | 3/2006 | Lahsinski et al. | 623/2.37 |
| 7,018,406 B2 | 3/2006 | Seguin et al. | 623/2.1 |
| 7,018,407 B1 | 3/2006 | Wright et al. | 623/2.11 |
| 7,018,408 B2 | 3/2006 | Bailey et al. | 623/2.11 |
| 7,022,134 B1 | 4/2006 | Quijano et al. | 623/1.24 |
| 7,025,780 B2 | 4/2006 | Gabbay | 623/2.13 |
| 7,033,390 B2 | 4/2006 | Johnson et al. | 623/2.11 |
| 7,037,333 B2 | 5/2006 | Myers et al. | 623/2.13 |
| 7,037,334 B1 | 5/2006 | Hlavka et al. | 623/2.36 |
| 7,041,128 B2 | 5/2006 | McGuckin, Jr. et al. | 623/1.36 |
| 7,041,132 B2 | 5/2006 | Quijano et al. | 623/2.11 |
| 7,044,966 B2 | 5/2006 | Svanidze et al. | 623/2.1 |
| 7,044,967 B1 | 5/2006 | Solem et al. | 623/2.36 |

| Patent/Pub No. | Date | Inventor(s) | Class |
|---|---|---|---|
| 7,048,754 B2 | 5/2006 | Martin et al. | 606/232 |
| 7,048,757 B2 | 5/2006 | Shaknovich | 623/1.24 |
| 7,052,487 B2 | 5/2006 | Cohn et al. | 604/509 |
| 7,052,507 B2 | 5/2006 | Wakuda et al. | 606/194 |
| 7,063,722 B2 | 6/2006 | Marquez | 623/2.36 |
| 7,066,954 B2 | 6/2006 | Ryan et al. | 623/2.36 |
| 7,070,616 B2 | 7/2006 | Majercak et al. | 623/1.24 |
| 7,070,618 B2 | 7/2006 | Streeter | 623/2.36 |
| 7,077,862 B2 | 7/2006 | Vidlund et al. | 623/2.36 |
| 7,081,131 B2 | 7/2006 | Thornton | 623/1.24 |
| 7,087,064 B1 | 8/2006 | Hyde | 606/142 |
| 7,089,051 B2 | 8/2006 | Jäverud et al. | 600/547 |
| 7,090,695 B2 | 8/2006 | Solem et al. | 623/2.37 |
| 2001/0011187 A1 | 8/2001 | Pavcnik et al. | |
| 2002/0177894 A1 | 11/2002 | Acosta et al. | 623/1.24 |
| 2002/0178570 A1 | 12/2002 | Sogard et al. | 29/516 |
| 2003/0055492 A1 | 3/2003 | Shaolian et al. | 623/1.24 |
| 2003/0130726 A1 | 7/2003 | Thorpe et al. | 623/1.24 |
| 2003/0229394 A1 | 12/2003 | Ogle et al. | 623/2.14 |
| 2003/0229395 A1 | 12/2003 | Cox | 623/2.36 |
| 2003/0233142 A1 | 12/2003 | Morales et al. | 623/2.37 |
| 2003/0236568 A1 | 12/2003 | Hojeibane et al. | 623/1.24 |
| 2003/0236569 A1 | 12/2003 | Mathis et al. | 623/1.26 |
| 2004/0002719 A1 | 1/2004 | Oz et al. | 606/142 |
| 2004/0003819 A1 | 1/2004 | St. Goar et al. | 128/898 |
| 2004/0010305 A1 | 1/2004 | Alferness et al. | 623/1.11 |
| 2004/0015230 A1 | 1/2004 | Moll et al. | 623/1.24 |
| 2004/0015232 A1 | 1/2004 | Shu et al. | 623/2.4 |
| 2004/0015233 A1 | 1/2004 | Jansen | 623/2.18 |
| 2004/0019374 A1 | 1/2004 | Hojeibane et al. | 623/1.13 |
| 2004/0019377 A1 | 1/2004 | Taylor et al. | 623/2.11 |
| 2004/0019378 A1 | 1/2004 | Hlavka et al. | 623/2.11 |
| 2004/0024447 A1 | 2/2004 | Haverich | 623/1.24 |
| 2004/0024451 A1 | 2/2004 | Johnson et al. | 623/2.11 |
| 2004/0024452 A1 | 2/2004 | Kruse et al. | 623/2.13 |
| 2004/0030321 A1 | 2/2004 | Fangrow, Jr. | 604/533 |
| 2004/0030381 A1 | 2/2004 | Shu | 623/2.1 |
| 2004/0030382 A1 | 2/2004 | St. Goar et al. | 623/2.36 |
| 2004/0030405 A1 | 2/2004 | Carpentier et al. | 623/23.72 |
| 2004/0034380 A1 | 2/2004 | Woolfson et al. | 606/170 |
| 2004/0034411 A1 | 2/2004 | Quijano et al. | 623/2.11 |
| 2004/0039436 A1 | 2/2004 | Spenser et al. | 623/1.13 |
| 2004/0039442 A1 | 2/2004 | St. Goar et al. | 623/2.36 |
| 2004/0039443 A1 | 2/2004 | Solem et al. | 623/2.37 |
| 2004/0044350 A1 | 3/2004 | Martin et al. | 606/139 |
| 2004/0044365 A1 | 3/2004 | Bachman | 606/213 |
| 2004/0044403 A1 | 3/2004 | Bischoff et al. | 623/1.41 |
| 2004/0049207 A1 | 3/2004 | Goldfarb et al. | 606/139 |
| 2004/0049211 A1 | 3/2004 | Tremulis et al. | 606/153 |
| 2004/0049266 A1 | 3/2004 | Anduiza et al. | 623/2.11 |
| 2004/0059351 A1 | 3/2004 | Eigler et al. | 606/148 |
| 2004/0059411 A1 | 3/2004 | Strecker | 623/1.23 |
| 2004/0059412 A1 | 3/2004 | Lytle, IV et al. | 623/2.11 |
| 2004/0060161 A1 | 4/2004 | Leal et al. | 29/558 |
| 2004/0073301 A1 | 4/2004 | Donlon et al. | 623/2.11 |
| 2004/0073302 A1 | 4/2004 | Rourke et al. | 623/2.36 |
| 2004/0078072 A1 | 4/2004 | Tu et al. | 623/1.23 |
| 2004/0078074 A1 | 4/2004 | Anderson et al. | 623/2.11 |
| 2004/0082910 A1 | 4/2004 | Constantz et al. | 604/101.04 |
| 2004/0082923 A1 | 4/2004 | Field | 604/267 |
| 2004/0082991 A1 | 4/2004 | Nguyen et al. | 623/2.14 |
| 2004/0087975 A1 | 5/2004 | Lucatero et al. | 606/139 |
| 2004/0088045 A1 | 5/2004 | Cox | 623/2.13 |
| 2004/0088046 A1 | 5/2004 | Speziali | 623/2.19 |
| 2004/0092858 A1 | 5/2004 | Wilson et al. | 604/9 |
| 2004/0093060 A1 | 5/2004 | Seguin et al. | 623/1.11 |
| 2004/0093070 A1 | 5/2004 | Hojeibane et al. | 623/1.15 |
| 2004/0093080 A1 | 5/2004 | Helmus et al. | 623/2.41 |
| 2004/0097979 A1 | 5/2004 | Svanidze et al. | 606/151 |
| 2004/0098098 A1 | 5/2004 | McGuckin, Jr. et al. | 623/1.14 |
| 2004/0098112 A1 | 5/2004 | DiMatteo et al. | 623/1.24 |
| 2004/0102839 A1 | 5/2004 | Cohn et al. | 623/2.11 |
| 2004/0102840 A1 | 5/2004 | Solem et al. | 623/2.11 |
| 2004/0102842 A1 | 5/2004 | Jansen | 623/2.38 |
| 2004/0106976 A1 | 6/2004 | Bailey et al. | 623/1.11 |
| 2004/0106990 A1 | 6/2004 | Spence et al. | 623/2.11 |
| 2004/0106991 A1 | 6/2004 | Hopkins et al. | 623/2.13 |
| 2004/0111096 A1 | 6/2004 | Tu et al. | 606/108 |
| 2004/0117009 A1 | 6/2004 | Cali et al. | 623/2.12 |
| 2004/0122448 A1 | 6/2004 | Levine | 606/139 |
| 2004/0122512 A1 | 6/2004 | Navia et al. | 623/2.12 |
| 2004/0122513 A1 | 6/2004 | Navia et al. | 623/2.12 |
| 2004/0122514 A1 | 6/2004 | Fogarty et al. | 623/2.14 |
| 2004/0122515 A1 | 6/2004 | Chu | 623/2.29 |
| 2004/0122516 A1 | 6/2004 | Fogarty et al. | 623/2.37 |
| 2004/0127979 A1 | 7/2004 | Wilson et al. | 623/2.1 |
| 2004/0127980 A1 | 7/2004 | Kowalsky et al. | 623/2.11 |
| 2004/0127981 A1 | 7/2004 | Rahdert et al. | 623/2.36 |
| 2004/0127982 A1 | 7/2004 | Machold et al. | 623/2.36 |
| 2004/0133220 A1 | 7/2004 | Lashinski et al. | 606/151 |
| 2004/0133267 A1 | 7/2004 | Lane | 623/1.24 |
| 2004/0133273 A1 | 7/2004 | Cox | 623/2.11 |
| 2004/0138742 A1 | 7/2004 | Myers et al. | 623/2.12 |
| 2004/0138743 A1 | 7/2004 | Myers et al. | 623/2.13 |
| 2004/0138744 A1 | 7/2004 | Lashinski et al. | 623/2.36 |
| 2004/0138745 A1 | 7/2004 | Macoviak et al. | 623/2.36 |
| 2004/0148018 A1 | 7/2004 | Carpentier et al. | 623/2.18 |
| 2004/0148019 A1 | 7/2004 | Vidlund et al. | 623/2.36 |
| 2004/0148020 A1 | 7/2004 | Vidlund et al. | 623/2.36 |
| 2004/0153052 A1 | 8/2004 | Mathis | 606/1 |
| 2004/0153146 A1 | 8/2004 | Lashinski et al. | 623/2.36 |
| 2004/0153147 A1 | 8/2004 | Mathis | 623/2.37 |
| 2004/0158321 A1 | 8/2004 | Reuter et al. | 623/2.36 |
| 2004/0162610 A1 | 8/2004 | Liska et al. | 623/2.11 |
| 2004/0167539 A1 | 8/2004 | Kuehn et al. | 606/108 |
| 2004/0167620 A1 | 8/2004 | Ortiz et al. | 623/2.11 |
| 2004/0172046 A1 | 9/2004 | Hlavka et al. | 606/142 |
| 2004/0176839 A1 | 9/2004 | Huynh et al. | 623/2.4 |
| 2004/0176840 A1 | 9/2004 | Langberg et al. | 623/2.37 |
| 2004/0181238 A1 | 9/2004 | Zarbatany et al. | 606/108 |
| 2004/0186444 A1 | 9/2004 | Daly et al. | 604/247 |
| 2004/0186558 A1 | 9/2004 | Pavcnik et al. | 623/1.24 |
| 2004/0186561 A1 | 9/2004 | McGuckin, Jr. et al. | 623/1.36 |
| 2004/0186563 A1 | 9/2004 | Iobbi | 623/2.11 |
| 2004/0186565 A1 | 9/2004 | Schreck | 623/2.18 |
| 2004/0186566 A1 | 9/2004 | Hindrichs et al. | 623/2.37 |
| 2004/0193191 A1 | 9/2004 | Starksen et al. | 606/153 |
| 2004/0193253 A1 | 9/2004 | Thorpe et al. | 623/1.24 |
| 2004/0193260 A1 | 9/2004 | Alferness et al. | 623/2.11 |
| 2004/0199155 A1 | 10/2004 | Mollenauer | 606/27 |
| 2004/0199183 A1 | 10/2004 | Oz et al. | 606/142 |
| 2004/0199191 A1 | 10/2004 | Schwartz | 606/159 |
| 2004/0204758 A1 | 10/2004 | Eberhardt et al. | 623/2.15 |
| 2004/0206363 A1 | 10/2004 | McCarthy et al. | 128/898 |
| 2004/0210240 A1 | 10/2004 | Saint | 606/139 |
| 2004/0210301 A1 | 10/2004 | Obermiller | 623/1.24 |
| 2004/0210303 A1 | 10/2004 | Sedransk | 623/2.1 |
| 2004/0210304 A1 | 10/2004 | Seguin et al. | 623/2.11 |
| 2004/0210305 A1 | 10/2004 | Shu et al. | 623/2.11 |
| 2004/0210306 A1 | 10/2004 | Quijano et al. | 623/2.17 |
| 2004/0210307 A1 | 10/2004 | Khairkhahan | 623/2.18 |
| 2004/0215333 A1 | 10/2004 | Duran et al. | 623/1.24 |
| 2004/0215339 A1 | 10/2004 | Drasler et al. | 623/3.1 |
| 2004/0220654 A1 | 11/2004 | Mathis et al. | 623/1.11 |
| 2004/0220657 A1 | 11/2004 | Nieminen et al. | 623/1.15 |
| 2004/0225322 A1 | 11/2004 | Garrison et al. | 606/200 |
| 2004/0225344 A1 | 11/2004 | Hoffa et al. | 623/1.1 |
| 2004/0225348 A1 | 11/2004 | Case et al. | 623/1.15 |
| 2004/0225352 A1 | 11/2004 | Osborne et al. | 623/1.24 |
| 2004/0225353 A1 | 11/2004 | McGuckin, Jr. et al. | 623/2.11 |
| 2004/0225354 A1 | 11/2004 | Allen et al. | 623/2.11 |
| 2004/0225355 A1 | 11/2004 | Stevens | 623/2.11 |
| 2004/0225356 A1 | 11/2004 | Frater | 623/2.14 |
| 2004/0230117 A1 | 11/2004 | Tosaya et al. | 600/439 |
| 2004/0230297 A1 | 11/2004 | Thornton | 623/1.24 |
| 2004/0236411 A1 | 11/2004 | Sarac et al. | 623/1.26 |

| | | | | | | | |
|---|---|---|---|---|---|---|---|
| 2004/0236418 A1 | 11/2004 | Stevens | 623/2.11 | 2005/0090846 A1 | 4/2005 | Pedersen et al. | 606/159 |
| 2004/0236419 A1 | 11/2004 | Milo | 623/2.36 | 2005/0096735 A1 | 5/2005 | Hojeibane et al. | 623/1.24 |
| 2004/0243153 A1 | 12/2004 | Liddicoat et al. | 606/151 | 2005/0096738 A1 | 5/2005 | Cali et al. | 623/2.18 |
| 2004/0243219 A1 | 12/2004 | Fischer et al. | 623/1.15 | 2005/0096739 A1 | 5/2005 | Cao | 623/2.19 |
| 2004/0243227 A1 | 12/2004 | Starksen et al. | 623/2.11 | 2005/0096740 A1 | 5/2005 | Langberg et al. | 623/2.36 |
| 2004/0243228 A1 | 12/2004 | Kowalsky et al. | 623/2.11 | 2005/0101975 A1 | 5/2005 | Nguyen et al. | 606/151 |
| 2004/0243230 A1 | 12/2004 | Navia et al. | 623/2.36 | 2005/0102026 A1 | 5/2005 | Turner et al. | 623/2.1 |
| 2004/0249452 A1 | 12/2004 | Adams et al. | 623/2.36 | 2005/0107810 A1 | 5/2005 | Morales et al. | 606/143 |
| 2004/0254600 A1 | 12/2004 | Zarbatany et al. | 606/194 | 2005/0107811 A1 | 5/2005 | Starksen et al. | 606/143 |
| 2004/0254636 A1 | 12/2004 | Flagle et al. | 623/1.24 | 2005/0107812 A1 | 5/2005 | Starksen et al. | 606/143 |
| 2004/0260276 A1 | 12/2004 | Rudko et al. | 606/15 | 2005/0107872 A1 | 5/2005 | Mensah et al. | 623/2.14 |
| 2004/0260317 A1 | 12/2004 | Bloom et al. | 606/151 | 2005/0113910 A1 | 5/2005 | Paniagua et al. | 623/2.14 |
| 2004/0260322 A1 | 12/2004 | Rudko et al. | 606/167 | 2005/0119673 A1 | 6/2005 | Gordon et al. | 606/151 |
| 2004/0260389 A1 | 12/2004 | Case et al. | 623/1.24 | 2005/0119734 A1 | 6/2005 | Spence et al. | 623/2.11 |
| 2004/0260390 A1 | 12/2004 | Sarac et al. | 623/1.24 | 2005/0119735 A1 | 6/2005 | Spence et al. | 623/2.36 |
| 2004/0260393 A1 | 12/2004 | Rahdert et al. | 623/2.36 | 2005/0125011 A1 | 6/2005 | Spence et al. | 606/144 |
| 2004/0260394 A1 | 12/2004 | Douk et al. | 623/2.36 | 2005/0131438 A1 | 6/2005 | Cohn | 606/170 |
| 2004/0267357 A1 | 12/2004 | Allen et al. | 623/2.11 | 2005/0137449 A1 | 6/2005 | Nieminen et al. | 600/37 |
| 2005/0004583 A1 | 1/2005 | Oz et al. | 606/142 | 2005/0137450 A1 | 6/2005 | Aronson et al. | 600/37 |
| 2005/0004667 A1 | 1/2005 | Swinford et al. | 623/2.36 | 2005/0137451 A1 | 6/2005 | Gordon et al. | 600/37 |
| 2005/0010285 A1 | 1/2005 | Lambrecht et al. | 623/2.18 | 2005/0137676 A1 | 6/2005 | Richardson et al. | 623/1.11 |
| 2005/0010287 A1 | 1/2005 | Macoviak et al. | 623/2.36 | 2005/0137681 A1 | 6/2005 | Shoemaker et al. | 623/1.23 |
| 2005/0015112 A1 | 1/2005 | Cohn et al. | 606/200 | 2005/0137682 A1 | 6/2005 | Justino | 623/1.24 |
| 2005/0021056 A1 | 1/2005 | St. Goar et al. | 606/144 | 2005/0137685 A1 | 6/2005 | Nieminen et al. | 623/2.11 |
| 2005/0021136 A1 | 1/2005 | Xie et al. | 623/2.14 | 2005/0137686 A1 | 6/2005 | Salahieh et al. | 623/2.11 |
| 2005/0027261 A1 | 2/2005 | Weaver et al. | 604/246 | 2005/0137688 A1 | 6/2005 | Salahieh et al. | 623/2.11 |
| 2005/0027348 A1 | 2/2005 | Case et al. | 623/1.24 | 2005/0137689 A1 | 6/2005 | Salahieh et al. | 623/2.11 |
| 2005/0027351 A1 | 2/2005 | Reuter et al. | 623/2.11 | 2005/0137690 A1 | 6/2005 | Salahieh et al. | 623/2.11 |
| 2005/0027353 A1 | 2/2005 | Alferness et al. | 623/2.11 | 2005/0137691 A1 | 6/2005 | Salahieh et al. | 623/2.11 |
| 2005/0033398 A1 | 2/2005 | Seguin | 623/1.11 | 2005/0137692 A1 | 6/2005 | Haug et al. | 623/2.11 |
| 2005/0033419 A1 | 2/2005 | Alferness et al. | 623/2.11 | 2005/0137693 A1 | 6/2005 | Haug et al. | 623/2.11 |
| 2005/0033446 A1 | 2/2005 | Deem et al. | 623/23.6 | 2005/0137694 A1 | 6/2005 | Haug et al. | 623/2.11 |
| 2005/0038506 A1 | 2/2005 | Webler et al. | 623/2.11 | 2005/0137696 A1 | 6/2005 | Salahieh et al. | 623/2.11 |
| 2005/0038507 A1 | 2/2005 | Alferness et al. | 623/2.11 | 2005/0137697 A1 | 6/2005 | Salahieh et al. | 623/2.11 |
| 2005/0043790 A1 | 2/2005 | Seguin | 623/2.18 | 2005/0137698 A1 | 6/2005 | Salahieh et al. | 623/2.11 |
| 2005/0043792 A1 | 2/2005 | Solem et al. | 623/2.36 | 2005/0137699 A1 | 6/2005 | Salahieh et al. | 623/2.11 |
| 2005/0049679 A1 | 3/2005 | Taylor et al. | 623/1.15 | 2005/0137700 A1 | 6/2005 | Spence et al. | 623/2.36 |
| 2005/0049692 A1 | 3/2005 | Numamoto et al. | 623/1.24 | 2005/0137701 A1 | 6/2005 | Salahieh et al. | 623/2.38 |
| 2005/0049696 A1 | 3/2005 | Siess et al. | 623/2.11 | 2005/0137702 A1 | 6/2005 | Haug et al. | 623/2.38 |
| 2005/0049697 A1 | 3/2005 | Sievers | 623/2.26 | 2005/0143807 A1 | 6/2005 | Pavcnik et al. | 623/1.24 |
| 2005/0054977 A1 | 3/2005 | Laird et al. | 604/96.01 | 2005/0143809 A1 | 6/2005 | Salahieh et al. | 623/2.11 |
| 2005/0055079 A1 | 3/2005 | Duran | 623/1.13 | 2005/0143810 A1 | 6/2005 | Dauner et al. | 623/2.12 |
| 2005/0055087 A1 | 3/2005 | Starksen | 623/2.11 | 2005/0143811 A1 | 6/2005 | Realyvasquez | 623/2.36 |
| 2005/0055088 A1 | 3/2005 | Liddicoat et al. | 623/2.11 | 2005/0149014 A1 | 7/2005 | Hauck et al. | 606/41 |
| 2005/0055089 A1 | 3/2005 | Macoviak et al. | 623/2.37 | 2005/0149179 A1 | 7/2005 | Mathis et al. | 623/2.11 |
| 2005/0060029 A1 | 3/2005 | Le et al. | 623/2.11 | 2005/0149180 A1 | 7/2005 | Mathis et al. | 623/2.11 |
| 2005/0060030 A1 | 3/2005 | Lashinski et al. | 623/2.37 | 2005/0149181 A1 | 7/2005 | Eberhardt | 623/2.14 |
| 2005/0065460 A1 | 3/2005 | Laird | 604/20 | 2005/0159810 A1 | 7/2005 | Filsoufi | 623/2.1 |
| 2005/0065550 A1 | 3/2005 | Starksen et al. | 606/219 | 2005/0159811 A1 | 7/2005 | Lane | 623/2.14 |
| 2005/0065594 A1 | 3/2005 | Dimatteo et al. | 623/1.24 | 2005/0165477 A1 | 7/2005 | Anduiza et al. | 623/2.11 |
| 2005/0065597 A1 | 3/2005 | Lansac | 623/2.11 | 2005/0165478 A1 | 7/2005 | Song | 623/2.22 |
| 2005/0070998 A1 | 3/2005 | Rourke et al. | 623/2.11 | 2005/0171472 A1 | 8/2005 | Lutter | 604/101.03 |
| 2005/0075584 A1 | 4/2005 | Cali | 600/587 | 2005/0171601 A1 | 8/2005 | Cosgrove et al. | 623/2.11 |
| 2005/0075659 A1 | 4/2005 | Realyvasquez et al. | 606/167 | 2005/0177227 A1 | 8/2005 | Heim et al. | 623/2.12 |
| 2005/0075662 A1 | 4/2005 | Pedersen et al. | 606/194 | 2005/0177228 A1 | 8/2005 | Solem et al. | 623/2.36 |
| 2005/0075712 A1 | 4/2005 | Biancucci et al. | 623/1.11 | 2005/0182483 A1 | 8/2005 | Osborne et al. | 623/1.24 |
| 2005/0075713 A1 | 4/2005 | Biancucci et al. | 623/1.11 | 2005/0184122 A1 | 8/2005 | Hlavka et al. | 227/175.1 |
| 2005/0075717 A1 | 4/2005 | Nguyen et al. | 623/1.26 | 2005/0187614 A1 | 8/2005 | Agnew | 623/1.24 |
| 2005/0075718 A1 | 4/2005 | Nguyen et al. | 623/1.26 | 2005/0187616 A1 | 8/2005 | Realyvasquez | 623/2.11 |
| 2005/0075719 A1 | 4/2005 | Bergheim | 623/1.26 | 2005/0187617 A1 | 8/2005 | Navia | 623/2.13 |
| 2005/0075720 A1 | 4/2005 | Nguyen et al. | 623/1.26 | 2005/0192606 A1 | 9/2005 | Paul, Jr. et al. | 606/159 |
| 2005/0075723 A1 | 4/2005 | Schroeder et al. | 623/2.1 | 2005/0192665 A1 | 9/2005 | Spenser et al. | 623/2.11 |
| 2005/0075724 A1 | 4/2005 | Svanidze et al. | 623/2.11 | 2005/0197692 A1 | 9/2005 | Pai et al. | 623/2.1 |
| 2005/0075725 A1 | 4/2005 | Rowe | 623/2.14 | 2005/0197693 A1 | 9/2005 | Pai et al. | 623/2.1 |
| 2005/0075726 A1 | 4/2005 | Svanidze et al. | 623/2.14 | 2005/0197694 A1 | 9/2005 | Pai et al. | 623/2.1 |
| 2005/0075728 A1 | 4/2005 | Nguyen et al. | 623/2.17 | 2005/0203549 A1 | 9/2005 | Realyvasquez | 606/142 |
| 2005/0075729 A1 | 4/2005 | Nguyen et al. | 623/2.18 | 2005/0203605 A1 | 9/2005 | Dolan | 623/1.11 |
| 2005/0075730 A1 | 4/2005 | Myers et al. | 623/2.18 | 2005/0203614 A1 | 9/2005 | Forster et al. | 623/2.11 |
| 2005/0075731 A1 | 4/2005 | Artof et al. | 623/2.18 | 2005/0203615 A1 | 9/2005 | Forster et al. | 623/2.11 |
| 2005/0080483 A1 | 4/2005 | Solem et al. | 623/2.11 | 2005/0203616 A1 | 9/2005 | Cribier | 623/2.11 |
| 2005/0085900 A1 | 4/2005 | Case et al. | 623/1.24 | 2005/0203617 A1 | 9/2005 | Forster et al. | 623/2.14 |
| 2005/0085903 A1 | 4/2005 | Lau | 623/2.11 | 2005/0203618 A1 | 9/2005 | Sharkawy et al. | 623/2.38 |
| 2005/0085904 A1 | 4/2005 | Lemmon | 623/2.11 | 2005/0216039 A1 | 9/2005 | Lederman | 606/144 |

| Publication No. | Date | Inventor | Class |
|---|---|---|---|
| 2005/0216077 A1 | 9/2005 | Mathis et al. | 623/2.11 |
| 2005/0216078 A1 | 9/2005 | Starksen et al. | 623/2.11 |
| 2005/0222675 A1 | 10/2005 | Sauter | 623/1.26 |
| 2005/0222678 A1 | 10/2005 | Lashinski et al. | 623/2.11 |
| 2005/0228422 A1 | 10/2005 | Machold et al. | 606/167 |
| 2005/0228479 A1 | 10/2005 | Pavcnik et al. | 623/1.11 |
| 2005/0228486 A1 | 10/2005 | Case et al. | 623/1.24 |
| 2005/0228494 A1 | 10/2005 | Marquez | 623/2.18 |
| 2005/0228495 A1 | 10/2005 | Macoviak | 623/2.18 |
| 2005/0228496 A1 | 10/2005 | Mensah et al. | 623/2.41 |
| 2005/0234541 A1 | 10/2005 | Hunt et al. | 623/1.24 |
| 2005/0234546 A1 | 10/2005 | Nugent et al. | 623/2.11 |
| 2005/0240200 A1 | 10/2005 | Bergheim | 606/108 |
| 2005/0240202 A1 | 10/2005 | Shennib et al. | 606/142 |
| 2005/0240255 A1 | 10/2005 | Schaeffer | 623/1.11 |
| 2005/0240259 A1 | 10/2005 | Sisken et al. | 623/1.36 |
| 2005/0240262 A1 | 10/2005 | White | 623/2.12 |
| 2005/0244460 A1 | 11/2005 | Alferiev et al. | 424/426 |
| 2005/0246013 A1 | 11/2005 | Gabbay | 623/2.1 |
| 2005/0251251 A1 | 11/2005 | Cribier | 623/2.11 |
| 2005/0256566 A1 | 11/2005 | Gabbay | 623/2.1 |
| 2005/0261704 A1 | 11/2005 | Mathis | 606/108 |
| 2005/0261759 A1 | 11/2005 | Lambrecht et al. | 623/1.26 |
| 2005/0267493 A1 | 12/2005 | Schreck et al. | 606/139 |
| 2005/0267560 A1 | 12/2005 | Bates | 623/1.1 |
| 2005/0267565 A1 | 12/2005 | Dave et al. | 623/1.15 |
| 2005/0267571 A1 | 12/2005 | Spence et al. | 623/2.11 |
| 2005/0267573 A9 | 12/2005 | Macoviak et al. | 623/2.36 |
| 2005/0267574 A1 | 12/2005 | Cohn et al. | 623/2.36 |
| 2005/0272969 A1 | 12/2005 | Alferness et al. | 600/37 |
| 2005/0273160 A1 | 12/2005 | Lashinski et al. | 623/1.25 |
| 2005/0278015 A1 | 12/2005 | Dave et al. | 623/1.38 |
| 2005/0283178 A1 | 12/2005 | Flagle et al. | 606/191 |
| 2005/0288779 A1 | 12/2005 | Shaoulian et al. | 623/2.37 |
| 2006/0000715 A1 | 1/2006 | Whitcher et al. | 205/80 |
| 2006/0004439 A1 | 1/2006 | Spenser et al. | 623/1.23 |
| 2006/0004442 A1 | 1/2006 | Spenser et al. | 623/2.11 |
| 2006/0009804 A1 | 1/2006 | Pederson | 607/2 |
| 2006/0009841 A1 | 1/2006 | McGuckin, Jr. et al. | 623/2.38 |
| 2006/0009842 A1 | 1/2006 | Huynh et al. | 623/2.41 |
| 2006/0013805 A1 | 1/2006 | Hebbel et al. | 424/93.21 |
| 2006/0013855 A1 | 1/2006 | Carpenter et al. | 424/423 |
| 2006/0015136 A1 | 1/2006 | Besselink | 606/200 |
| 2006/0015178 A1 | 1/2006 | Moaddeb et al. | 623/2.36 |
| 2006/0015179 A1 | 1/2006 | Bulman-Fleming et al. | 623/2.36 |
| 2006/0020275 A1 | 1/2006 | Goldfarb et al. | 606/151 |
| 2006/0020327 A1 | 1/2006 | Lashinski et al. | 623/1.25 |
| 2006/0020332 A1 | 1/2006 | Lashinski et al. | 623/2.11 |
| 2006/0020334 A1 | 1/2006 | Lashinski et al. | 623/2.11 |
| 2006/0020335 A1 | 1/2006 | Kowalsky et al. | 623/2.36 |
| 2006/0020336 A1 | 1/2006 | Liddicoat | 623/2.37 |
| 2006/0025750 A1 | 2/2006 | Startksen et al. | 604/510 |
| 2006/0025784 A1 | 2/2006 | Startksen et al. | 606/151 |
| 2006/0025787 A1 | 2/2006 | Morales et al. | 606/151 |
| 2006/0025854 A1 | 2/2006 | Lashinski et al. | 623/1.25 |
| 2006/0025855 A1 | 2/2006 | Lashinski et al. | 623/2.1 |
| 2006/0025856 A1 | 2/2006 | Ryan et al. | 623/2.11 |
| 2006/0025857 A1 | 2/2006 | Bergheim et al. | 623/2.18 |
| 2006/0030747 A1 | 2/2006 | Kantrowitz et al. | 600/16 |
| 2006/0030866 A1 | 2/2006 | Schreck | 606/139 |
| 2006/0030882 A1 | 2/2006 | Adams et al. | 606/219 |
| 2006/0030885 A1 | 2/2006 | Hyde | 606/232 |
| 2006/0036317 A1 | 2/2006 | Vidlund et al. | 623/2.36 |
| 2006/0041305 A1 | 2/2006 | Lauterjung | 623/1.36 |
| 2006/0041306 A1 | 2/2006 | Vidlund et al. | 623/2.11 |
| 2006/0047297 A1 | 3/2006 | Case | 606/194 |
| 2006/0047338 A1 | 3/2006 | Jenson | 623/2.11 |
| 2006/0047343 A1 | 3/2006 | Oviatt et al. | 623/915 |
| 2006/0052804 A1 | 3/2006 | Mialhe | 606/157 |
| 2006/0052867 A1 | 3/2006 | Revuelta et al. | 623/2.18 |
| 2006/0058817 A1 | 3/2006 | Starksen et al. | 606/142 |
| 2006/0058865 A1 | 3/2006 | Case et al. | 623/1.11 |
| 2006/0058871 A1 | 3/2006 | Zakay et al. | 623/2.18 |
| 2006/0058889 A1 | 3/2006 | Case et al. | 623/23.68 |
| 2006/0064115 A1 | 3/2006 | Allen et al. | 606/139 |
| 2006/0064116 A1 | 3/2006 | Allen et al. | 606/139 |
| 2006/0064118 A1 | 3/2006 | Kimblad | 606/151 |
| 2006/0064174 A1 | 3/2006 | Zadno | 623/23.68 |
| 2006/0069400 A1 | 3/2006 | Burnett et al. | 606/153 |
| 2006/0069429 A1 | 3/2006 | Spence et al. | 623/2.11 |
| 2006/0069430 A9 | 3/2006 | Rahdert et al. | 623/2.36 |
| 2006/0074483 A1 | 4/2006 | Schrayer | 623/2.1 |
| 2006/0074484 A1 | 4/2006 | Huber | 623/2.11 |
| 2006/0074485 A1 | 4/2006 | Realyvasquez | 623/2.11 |
| 2006/0085060 A1 | 4/2006 | Campbell | 623/1.26 |
| 2006/0089708 A1 | 4/2006 | Osse et al. | 623/1.24 |
| 2006/0095115 A1 | 5/2006 | Bladillah et al. | 623/1.16 |
| 2006/0095125 A1 | 5/2006 | Chinn et al. | 623/2.4 |
| 2006/0099326 A1 | 5/2006 | Keogh et al. | 427/2.36 |
| 2006/0100697 A1 | 5/2006 | Casanova | 623/2.11 |
| 2006/0100699 A1 | 5/2006 | Vidlund et al. | 623/2.36 |
| 2006/0106278 A1 | 5/2006 | Machold et al. | 600/37 |
| 2006/0106279 A1 | 5/2006 | Machold et al. | 600/37 |
| 2006/0106456 A9 | 5/2006 | Machold et al. | 623/2.36 |
| 2006/0111660 A1 | 5/2006 | Wolf et al. | 604/9 |
| 2006/0111773 A1 | 5/2006 | Rittgers et al. | 623/1.24 |
| 2006/0111774 A1 | 5/2006 | Samkov et al. | 623/2.25 |
| 2006/0116572 A1 | 6/2006 | Case | 600/424 |
| 2006/0116756 A1 | 6/2006 | Solem et al. | 623/2.11 |
| 2006/0122686 A1 | 6/2006 | Gilad et al. | 623/1.13 |
| 2006/0122692 A1 | 6/2006 | Gilad et al. | 623/1.24 |
| 2006/0122693 A1 | 6/2006 | Biadillah et al. | 623/1.24 |
| 2006/0127443 A1 | 6/2006 | Helmus | 424/423 |
| 2006/0129235 A1 | 6/2006 | Seguin et al. | 623/2.11 |
| 2006/0129236 A1 | 6/2006 | McCarthy | 623/2.36 |
| 2006/0135476 A1 | 6/2006 | Kutryk et al. | 514/59 |
| 2006/0135964 A1 | 6/2006 | Vesely | 606/108 |
| 2006/0135967 A1 | 6/2006 | Realyvasquez | 606/142 |
| 2006/0136044 A1 | 6/2006 | Osborne | 623/1.24 |
| 2006/0136045 A1 | 6/2006 | Flagle et al. | 623/1.24 |
| 2006/0136052 A1 | 6/2006 | Vesely | 623/2.18 |
| 2006/0136054 A1 | 6/2006 | Berg et al. | 623/2.38 |
| 2006/0142846 A1 | 6/2006 | Pavcnik et al. | 623/1.24 |
| 2006/0142847 A1 | 6/2006 | Shaknovich | 623/1.24 |
| 2006/0142848 A1 | 6/2006 | Gabbay | 623/1.26 |
| 2006/0142854 A1 | 6/2006 | Alferness et al. | 623/2.11 |
| 2006/0149358 A1 | 7/2006 | Zilla et al. | 623/1.22 |
| 2006/0149360 A1 | 7/2006 | Schwammenthal et al. | 623/1.24 |
| 2006/0149367 A1 | 7/2006 | Sieracki | 623/2.21 |
| 2006/0149368 A1 | 7/2006 | Spence | 623/2.37 |
| 2006/0161133 A1 | 7/2006 | Laird et al. | 604/509 |
| 2006/0161248 A1 | 7/2006 | Case et al. | 623/2.1 |
| 2006/0161249 A1 | 7/2006 | Realyvasquez et al. | 623/2.11 |
| 2006/0161250 A1 | 7/2006 | Shaw | 623/2.17 |
| 2006/0167468 A1 | 7/2006 | Gabbay | 606/108 |
| 2006/0167541 A1 | 7/2006 | Lattouf | 623/2.11 |
| 2006/0167542 A1 | 7/2006 | Quintessenza | 623/2.12 |
| 2006/0167543 A1 | 7/2006 | Bailey et al. | 623/2.18 |

FOREIGN PATENT DOCUMENTS

| | | |
|---|---|---|
| WO | WO/02/41764 | 5/2002 |
| WO | WO 2004/016200 | 2/2004 |
| WO | WO 2004/019825 | 3/2004 |
| WO | WO 2004/021893 | 3/2004 |
| WO | WO 2004/023980 | 3/2004 |
| WO | WO 2004/030568 | 4/2004 |
| WO | WO 2004/030569 | 4/2004 |
| WO | WO 2004/030570 | 4/2004 |
| WO | WO 2004/032724 | 4/2004 |
| WO | WO 2004/032796 | 4/2004 |
| WO | WO 2004/037128 | 5/2004 |
| WO | WO 2004/037317 | 5/2004 |
| WO | WO 2004/039432 | 5/2004 |
| WO | WO 2004/043265 | 5/2004 |

| | | | | | | |
|---|---|---|---|---|---|---|
| WO | WO 2004/043273 | 5/2004 | | WO | WO 2005/046528 | 5/2005 |
| WO | WO 2004/043293 | 5/2004 | | WO | WO 2005/046529 | 5/2005 |
| WO | WO 2004/045370 | 6/2004 | | WO | WO 2005/046530 | 5/2005 |
| WO | WO 2004/045378 | 6/2004 | | WO | WO 2005/046531 | 5/2005 |
| WO | WO 2004/045463 | 6/2004 | | WO | WO 2005/048883 | 6/2005 |
| WO | WO 2004/047677 | 6/2004 | | WO | WO 2005/049103 | 6/2005 |
| WO | WO 2004/060217 | 7/2004 | | WO | WO 2005/051226 | 6/2005 |
| WO | WO 2004/060470 | 7/2004 | | WO | WO 2005/055811 | 6/2005 |
| WO | WO 2004/062725 | 7/2004 | | WO | WO 2005/055883 | 6/2005 |
| WO | WO 2004/066803 | 8/2004 | | WO | WO 2005/058206 | 6/2005 |
| WO | WO 2004/066826 | 8/2004 | | WO | WO 2005/065585 | 7/2005 |
| WO | WO 2004/069287 | 8/2004 | | WO | WO 2005/065593 | 7/2005 |
| WO | WO2004/075789 | 9/2004 | | WO | WO 2005/065594 | 7/2005 |
| WO | WO2004/080352 | 9/2004 | | WO | WO 2005/070342 | 8/2005 |
| WO | WO2004/082523 | 9/2004 | | WO | WO 2005/070343 | 8/2005 |
| WO | WO2004/082527 | 9/2004 | | WO | WO 2005/072654 | 8/2005 |
| WO | WO2004/082528 | 9/2004 | | WO | WO 2005/072655 | 8/2005 |
| WO | WO2004/082536 | 9/2004 | | WO | WO 2005/079706 | 9/2005 |
| WO | WO2004/082537 | 9/2004 | | WO | WO 2005/082288 | 9/2005 |
| WO | WO2004/082538 | 9/2004 | | WO | WO 2005/082289 | 9/2005 |
| WO | WO2004/082757 | 9/2004 | | WO | WO 2005/084595 | 9/2005 |
| WO | WO 2004/084746 | 10/2004 | | WO | WO 2005/087139 | 9/2005 |
| WO | WO 2004/084770 | 10/2004 | | WO | WO 2005/087140 | 9/2005 |
| WO | WO 2004/089246 | 10/2004 | | WO | WO 2006/000763 | 1/2006 |
| WO | WO 2004/089250 | 10/2004 | | WO | WO 2006/000776 | 1/2006 |
| WO | WO 2004/089253 | 10/2004 | | WO | WO 2006/002492 | 1/2006 |
| WO | WO 2004/091449 | 10/2004 | | WO | WO 2006/004679 | 1/2006 |
| WO | WO 2004/091454 | 10/2004 | | WO | WO 2006/005015 | 1/2006 |
| WO | WO 2004/093638 | 11/2004 | | WO | WO 2006/009690 | 1/2006 |
| WO | WO 2004/093726 | 11/2004 | | WO | WO 2006/011127 | 2/2006 |
| WO | WO 2004/093728 | 11/2004 | | WO | WO 2006/012011 | 2/2006 |
| WO | WO 2004/093730 | 11/2004 | | WO | WO 2006/012013 | 2/2006 |
| WO | WO 2004/093745 | 11/2004 | | WO | WO 2006/012038 | 2/2006 |
| WO | WO 2004/093935 | 11/2004 | | WO | WO 2006/012068 | 2/2006 |
| WO | WO 2004/096100 | 11/2004 | | WO | WO 2006/012322 | 2/2006 |
| WO | WO 2004/103222 | 12/2004 | | WO | WO 2006/019498 | 2/2006 |
| WO | WO 2004/103223 | 12/2004 | | WO | WO 2006/026371 | 3/2006 |
| WO | WO 2004/105584 | 12/2004 | | WO | WO 2006/026377 | 3/2006 |
| WO | WO 2004/105651 | 12/2004 | | WO | WO 2006/026912 | 3/2006 |
| WO | WO 2004/112582 | 12/2004 | | WO | WO 2006/027499 | 3/2006 |
| WO | WO 2004/112585 | 12/2004 | | WO | WO 2006/028821 | 3/2006 |
| WO | WO 2004/112643 | 12/2004 | | WO | WO 2006/029062 | 3/2006 |
| WO | WO 2004/112652 | 12/2004 | | WO | WO 2006/031436 | 3/2006 |
| WO | WO 2004/112657 | 12/2004 | | WO | WO 2006/031469 | 3/2006 |
| WO | WO 2004/112658 | 12/2004 | | WO | WO 2006/032051 | 3/2006 |
| WO | WO 2005/000152 | 1/2005 | | WO | WO 2006/034245 | 3/2006 |
| WO | WO 2005/002424 | 1/2005 | | WO | WO 2006/035415 | 4/2006 |
| WO | WO 2005/002466 | 1/2005 | | WO | WO 2006/041505 | 4/2006 |
| WO | WO 2005/004753 | 1/2005 | | WO | WO 2006/044679 | 4/2006 |
| WO | WO 2005/007017 | 1/2005 | | WO | WO 2006/048664 | 5/2006 |
| WO | WO 2005/007018 | 1/2005 | | WO | WO 2006/050459 | 5/2006 |
| WO | WO 2005/007036 | 1/2005 | | WO | WO 2006/050460 | 5/2006 |
| WO | WO 2005/007037 | 1/2005 | | WO | WO 2006/054107 | 5/2006 |
| WO | WO 2005/009285 | 2/2005 | | WO | WO 2006/054930 | 5/2006 |
| WO | WO 2005/009286 | 2/2005 | | WO | WO 2006/055982 | 5/2006 |
| WO | WO 2005/009505 | 2/2005 | | WO | WO 2006/060546 | 6/2006 |
| WO | WO 2005/009506 | 2/2005 | | WO | WO 2006/063108 | 6/2006 |
| WO | WO 2005/011473 | 2/2005 | | WO | WO 2006/063181 | 6/2006 |
| WO | WO 2005/011534 | 2/2005 | | WO | WO 2006/063199 | 6/2006 |
| WO | WO 2005/011535 | 2/2005 | | WO | WO 2006/064490 | 6/2006 |
| WO | WO 2005/013860 | 2/2005 | | WO | WO 2006/065212 | 6/2006 |
| WO | WO 2005/018507 | 3/2005 | | WO | WO 2006/065930 | 6/2006 |
| WO | WO 2005/021063 | 3/2005 | | WO | WO 2006/066148 | 6/2006 |
| WO | WO 2005/023155 | 3/2005 | | WO | WO 2006/066150 | 6/2006 |
| WO | WO 2005/025644 | 3/2005 | | WO | WO 2006/069094 | 6/2006 |
| WO | WO 2005/027790 | 3/2005 | | WO | WO 2006/070372 | 7/2006 |
| WO | WO 2005/027797 | 3/2005 | | WO | WO 2006/073628 | 7/2006 |
| WO | WO 2005/034812 | 4/2005 | | WO | WO 2006/076890 | 7/2006 |
| WO | WO 2005/039428 | 5/2005 | | | | |
| WO | WO 2005/039452 | 5/2005 | | | | |
| WO | WO 2005/046488 | 5/2005 | | | | |

OTHER PUBLICATIONS

US 6,723,117, 04/2004, Menz et al. (withdrawn)

METHODS FOR VENOUS VALVE REPLACEMENT WITH A CATHETER

FIELD OF THE INVENTION

The present invention relates generally to apparatus, systems, and methods for use in the vasculature; and more particularly to venous valve apparatus, systems, and methods for use in the peripheral vasculature.

BACKGROUND OF THE INVENTION

The venous system of the legs uses pumps to help return blood to the heart. These pumps are formed from the combined action of various muscle groups and bicuspid one-way valves within the venous vasculature. Venous valves create one way flow to prevent blood from flowing away from the heart and also serve to reduce hydrostatic pressure in the lower legs. When valves fail, blood can pool in the lower legs resulting in swelling and ulcers of the leg. The absence of functioning venous valves can lead to chronic venous insufficiency. Venous insufficiency is a condition in which the veins fail to return blood efficiently to the heart. This condition usually involves one or more of the deep veins. Symptoms include swelling of the legs and pain in the extremities such as a dull aching, heaviness, or cramping.

Techniques for both repairing and replacing the valves exist, but are tedious and require invasive surgical procedures. Direct and indirect valvuoplasty procedures are used to repair damaged valves. Transposition and transplantation are used to replace an incompetent valve. Transposition involves moving a vein with an incompetent valve to a site with a competent valve. Transplantation replaces an incompetent valve with a harvested valve from another venous site. Valves can be transplanted into the venous system, but current devices are not successful enough to see widespread usage.

DETAILED DESCRIPTION

Figure 1A:
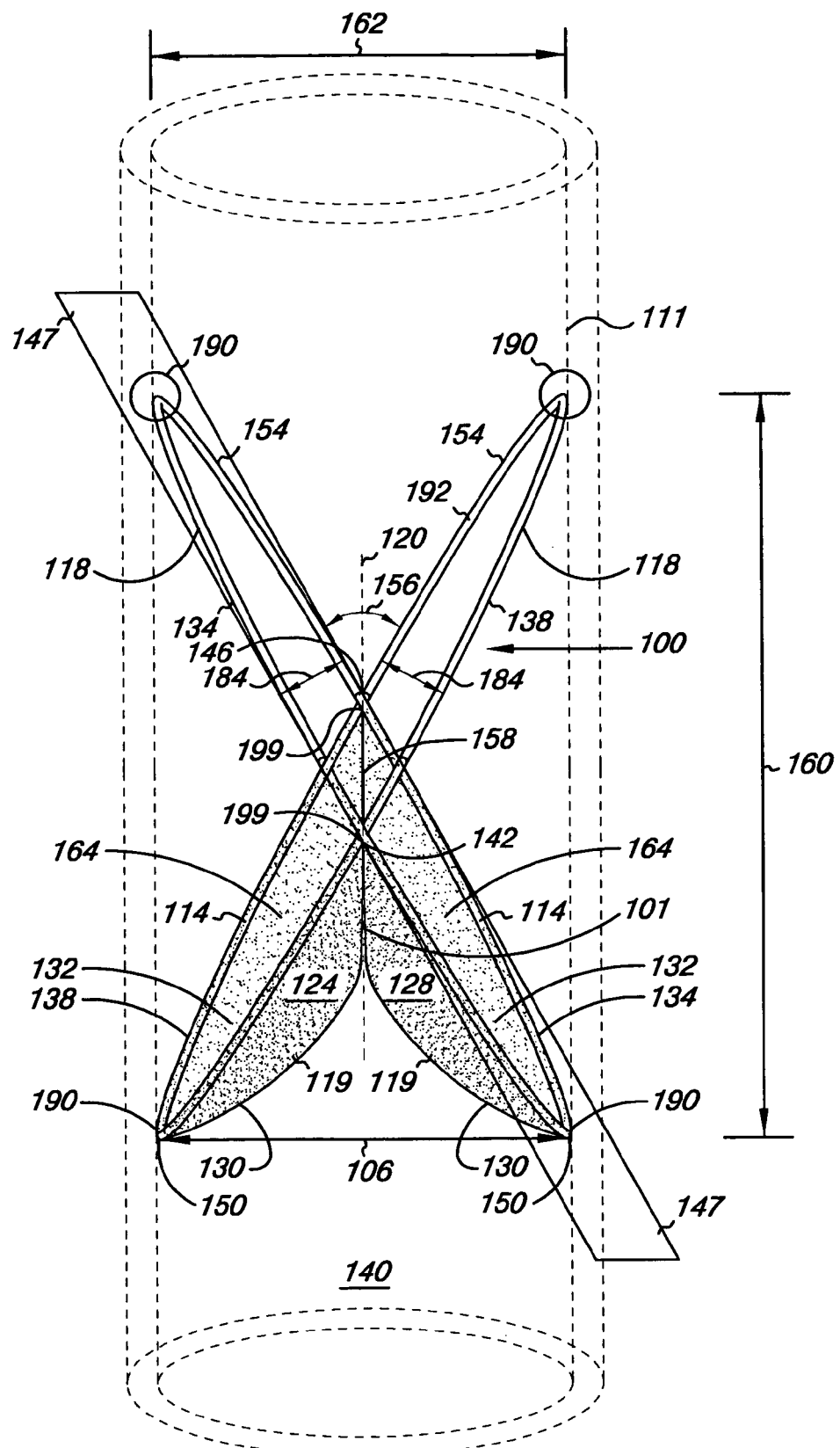
FIGS. 1A and 1B illustrate an embodiment of a valve.

Embodiments of the present invention are directed to an apparatus, system, and method for valve replacement. For example, the apparatus can include a valve that can be used to replace an incompetent valve in a body lumen. Embodiments of the valve can include a frame and leaflet material that can be implanted through minimally-invasive techniques into the body lumen near an incompetent valve. Embodiments of the apparatus, system, and method for valve replacement may help to maintain antegrade blood flow, while decreasing retrograde blood flow and reduce hydrostatic pressure in a venous system of individuals having venous insufficiency, such as venous insufficiency in the legs.

The Figures herein follow a numbering convention in which the first digit or digits correspond to the drawing Figure number and the remaining digits identify an element or component in the drawing. Similar elements or components between different Figures may be identified by the use of similar digits. For example, 110 may reference element "10" in FIG. 1, and a similar element may be referenced as 210 in FIG. 2.

FIGS. 1-4 provide illustrations of various embodiments of a valve of the present invention. Generally, valves can be implanted within the fluid passageway of a body lumen, such as for replacement of a valve structure within the body lumen (e.g., a venous valve), to regulate the flow of a bodily fluid through the body lumen in a single direction. Elements shown in the various embodiments herein can be added, exchanged, and/or eliminated so as to provide any number of additional embodiments of a valve.

Figure 1B:
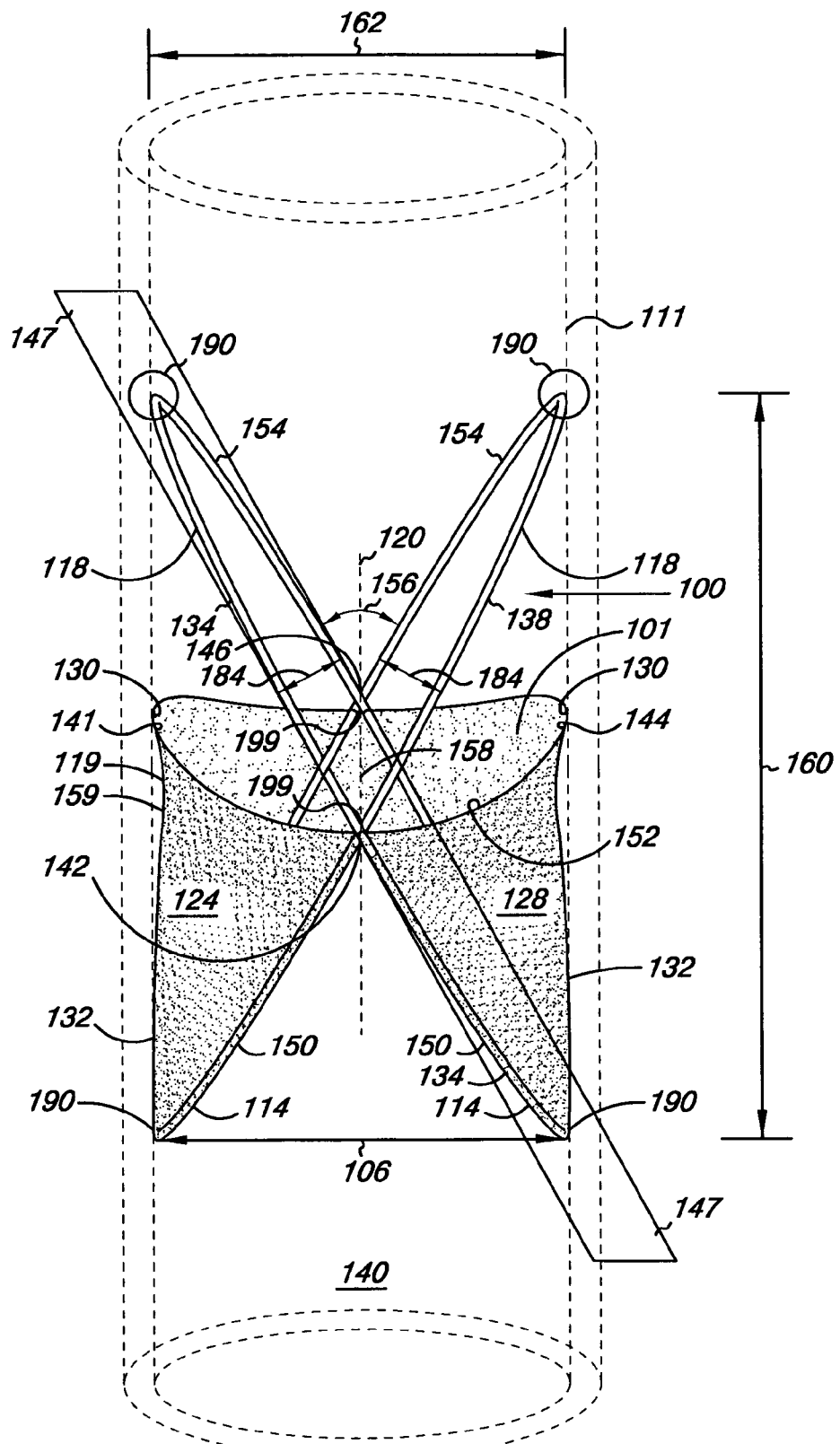

FIGS. 1A and 1B illustrate one embodiment of a valve 100. Valve 100 includes a valve frame 114, a support frame 118, and valve leaflets 119. Valve frame 114 and support frame 118 of valve 100 meet on an axis 120. As discussed herein, valve frame 114 and support frame 118 extend from axis 120 in an opposing direction and meet so as to form a flexible joint at and/or around axis 120 according to a number of embodiments.

Multiple embodiments exist for valve frame 114 and support frame 118, both of which can include any number of structural configurations. Generally, the valve frame 114 and the support frame 118 can have curved structural configurations, as will be discussed herein. For example, valve frame 114 and support frame 118 can include a first elliptical member 134 and a second elliptical member 138, as illustrated in FIGS. 1 and 2.

The first elliptical member 134 and the second elliptical member 138 meet at a first region 142 and a second region 146, where the first region 142 and the second region 146 are opposite each other across axis 120. The first region 142 and the second region 146 can be located at any number of locations along the first elliptical member 134 and the second elliptical member 138. For example, the first region 142 and the second region 146 can be at or near a minor axis of the first elliptical member 134 and the second elliptical member 138. In an additional embodiment, the first region 142 and the second region 146 can be positioned away from the minor axis of the first elliptical member 134 and the second elliptical member 138.

While the term elliptical member is used herein, other shapes are possible for the structural members that help to form a valve of the present invention. For example, the valve frame 114 and the support frame 118 can include circular members that meet at the first region 142 and the second region 146. In one embodiment, the circular members meet at the first region 142 and the second region 146 at, or about, the diameter of the circular members. In an additional embodiment, the first region 142 and the second region 146 can be positioned away from the diameter of the circular members. Other shapes besides elliptical and circular are also possible.

The first elliptical member 134 and the second elliptical member 138 can also include either a planar or a non-planar configuration, as will be discussed herein. For example, FIGS. 1A and 1B illustrate an embodiment in which the first elliptical member 134 and the second elliptical member 138 have a planar configuration 147. As such, the first elliptical member 134 and the second elliptical member 138 each form a portion of the valve frame 114 and the support frame 118. For example, the first elliptical member 134 and the second elliptical member 138 both include a valve portion 150 and a support portion 154. The valve portion 150 of the first elliptical member 134 and the second elliptical member 138 extend from the first region 142 and the second region 146 to form the valve frame 114. Similarly, the support portion 154 of the first elliptical member 134 and the second elliptical member 138 extend from the first region 142 and the second region 146 to form the support frame 118.

The first elliptical member 134 and the second elliptical member 138 meet at the first region 142 and the second region 146 at an angle 156. In one embodiment, the size of angle 156 can be selected based upon the type of body lumen and the body lumen size in which the valve 100 is to be placed. In an additional embodiment, there can also be a minimum diameter 158 between the first region 142 and the second region 146 that ensures that the first elliptical member 134 and the second elliptical member 138 will have an appropriate expansion force against the inner wall of the body lumen in which the valve 100 is being placed.

Additional factors include, but are not limited to, a longitudinal length 160 and a width 162 of the valve 100. These factors, along with others discussed herein, can be used to provide the angle 156 that is sufficient to ensure that the first elliptical member 134 and the second elliptical member 138 have an appropriate expansion force against an inner wall of the body lumen in which the valve 100 is being placed. For example, the minimum diameter 158 between the first region 142 and the second region 146 and the angle 156 can both be selected to provide an essentially equivalent expansion force on the body lumen 111 at, or around, the first region 142, the second region 146, and by the other portions of the first elliptical member 134 and the second elliptical member 138 that contact the body lumen 111.

The ability of the valve frame 114 and the support frame 118 to form a flexible joint at and/or around axis 120 allows the valve 100 to accommodate changes in body lumen size (e.g., diameter of the body lumen) by increasing or decreasing angle 156. In addition, the valve frame 114 and the support frame 118 also have the ability to flex, as discussed herein, to allow for the distance between the first region 142 and the second region 146 to increase or decrease, thereby further accommodating changes in the body lumen size (e.g., diameter of the body lumen). The valve frame 114 and the support frame 118 can also provide sufficient contact and expansion force with the surface of a body lumen wall to encourage fixation of the valve 100 and to prevent retrograde flow within the body lumen.

Figure 2A:
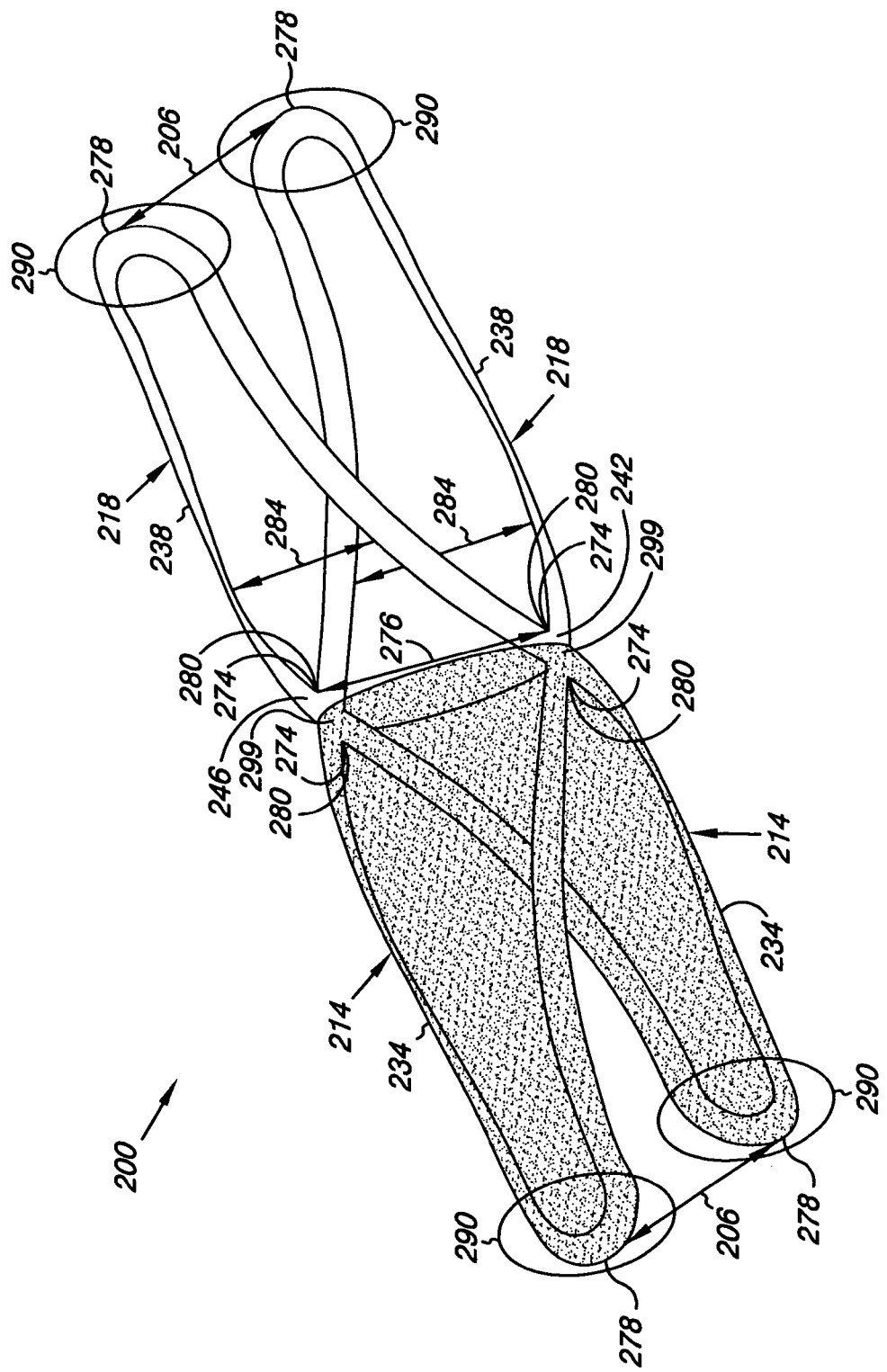
FIGS. 2A and 2B illustrate an embodiment of a valve in an open configuration and an exploded view of the valve.
Figure 2B:
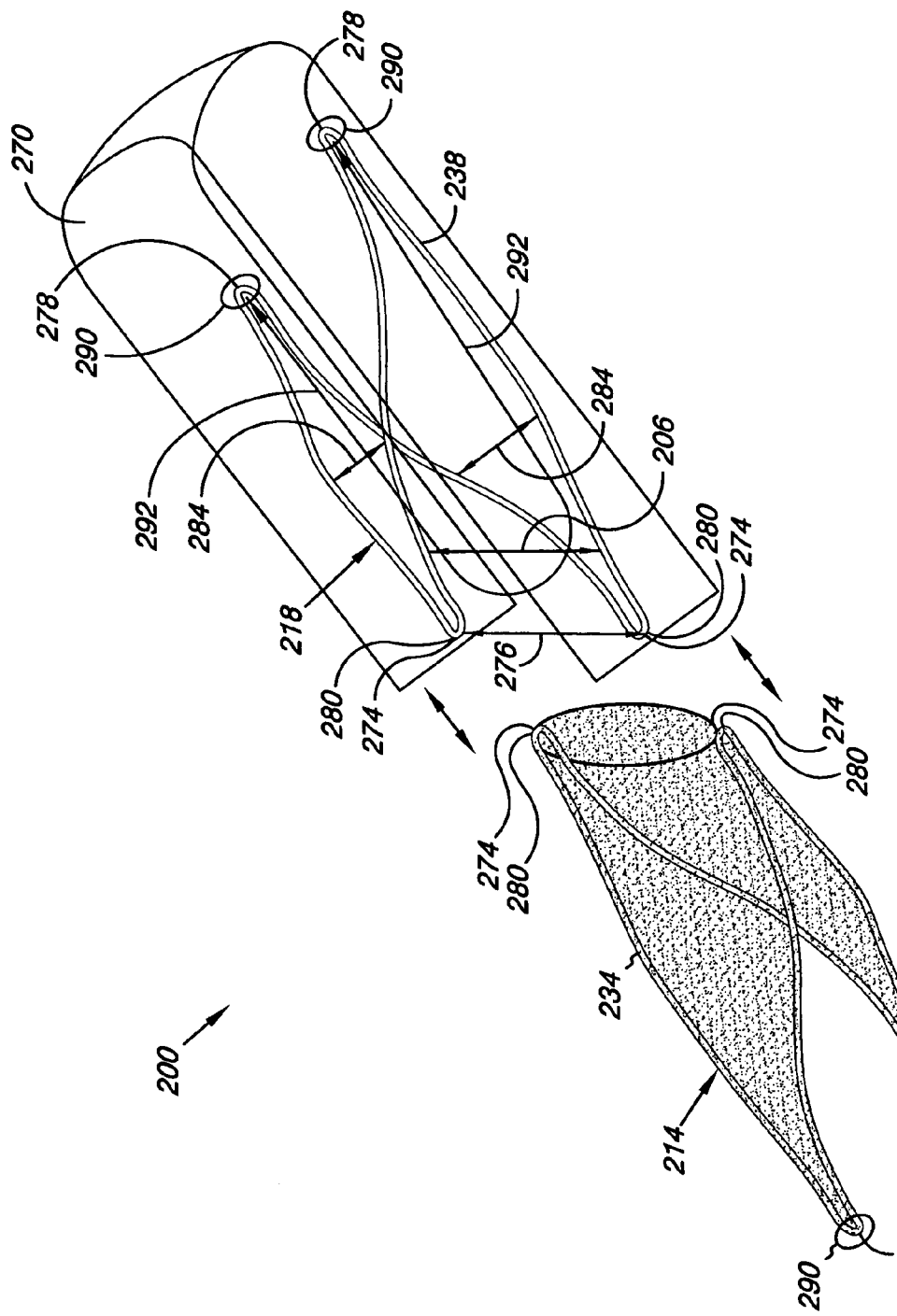

FIGS. 2A and 2B provide a further illustration of a valve 200. FIG. 2B illustrates an exploded view of valve 200, where the first elliptical member 234 and the second elliptical member 238 are shown separated so as to better illustrate a non-planar configuration 270 of the elliptical members 234 and 238. In one embodiment, the first elliptical member 234 and the second elliptical member 238 can have a non-planar configuration 270, where the first elliptical member 234 can form the valve frame 214, and the second elliptical member 238 can form the support frame 218. For example, the non-planar configuration 270 of the first elliptical member 234 and the second elliptical member 238 can include a curve 274 at, or near the minor axis 276, to provide for a series of alternating convex curves 278 and concave curves 280. In another embodiment, the curve 274 need not be located at, or about, the minor axis 276 of the first elliptical member 234 and the second elliptical member 238.

Figure 3:
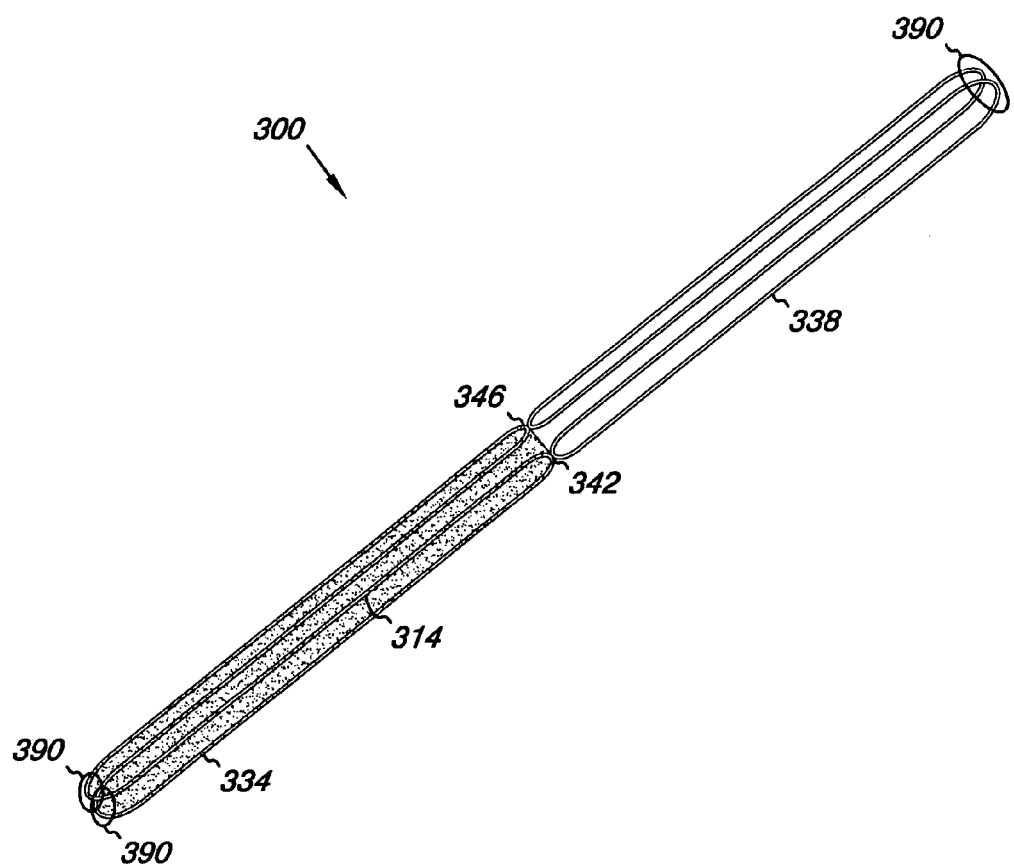
FIG. 3 illustrates an embodiment of a valve in a compressed state.
Figure 4:
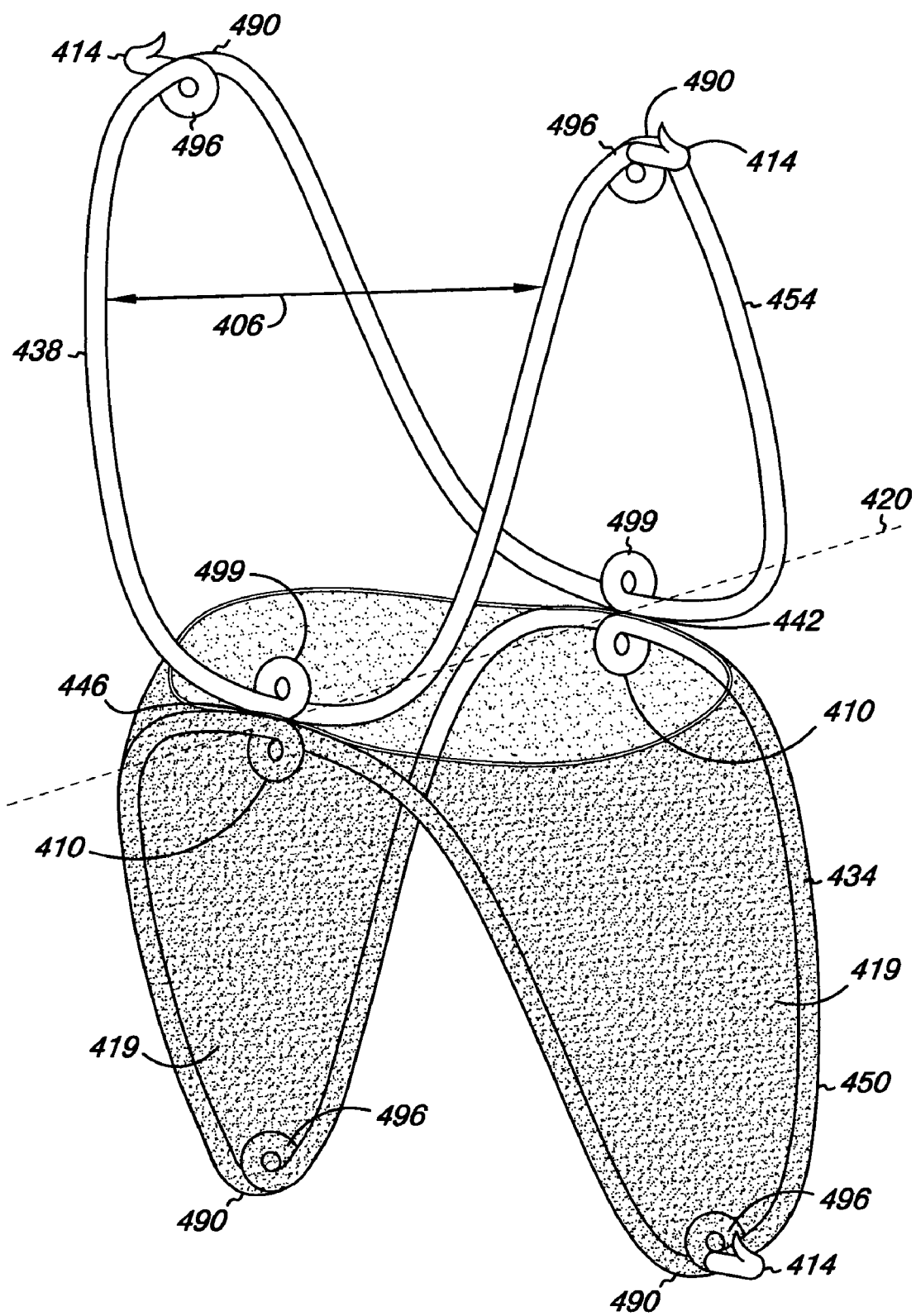
FIG. 4 illustrates an embodiment of a valve in an open configuration.

The curved structural configuration of the valve frame 214 and the support frame 218 allow for valve 200 to repeatably travel between a collapsed state, as shown in FIG. 3, and an expanded state, as shown in FIGS. 1, 2, and 4 along a first travel path 284. For example, the first elliptical member 234 and the second elliptical member 238 include an elastic region 290, at or adjacent a major axis 292 of the first elliptical member 234 and the second elliptical member 238. The elastic region 290 allows the first elliptical member 234 and the second elliptical member 238 to travel along the first travel path 284, so as to change a length of the minor axis 276 of the first elliptical member 234 and the second elliptical member 238.

Figure 5A:
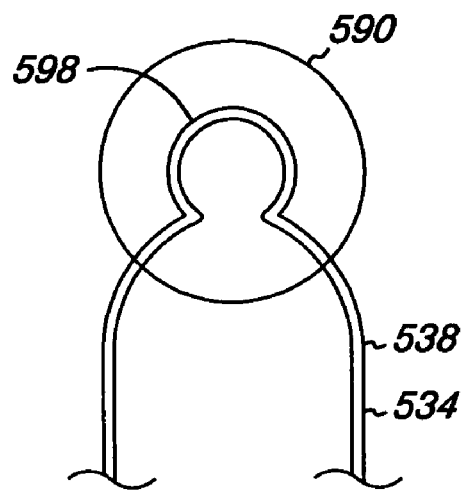
FIGS. 5A and 5B illustrate embodiments of elastic regions for valves.
Figure 5B:
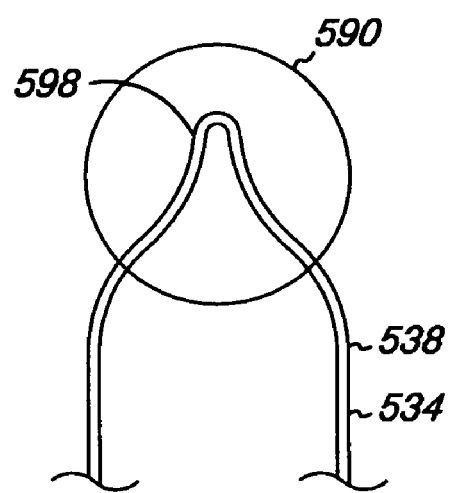

FIG. 4 illustrates one embodiment in which the elastic region 490 can include an integrated spring 496. For example, the first elliptical member 434 and the second elliptical member 438 can each include the integrated spring 496 in the valve portion 450 and the support portion 454 of the first elliptical member 434 and the second elliptical member 438. In one embodiment, the integrated spring 496 can have a circular or an elliptical coil configuration. FIGS. 5A and 5B provide additional embodiments of elastic region 590, were elastic region 590 can include a protuberance 598 in the first elliptical member 534 and the second elliptical member 538. Other shapes for the elastic region are also possible.

Referring again to FIGS. 2A and 2B, the valve frame 214 and the support frame 218 meet at the first region 242 and the second region 246. The valve frame 214 and the support frame 218 meet in the first region 242 and the second region 246 at a flexible connection joint 299. The flexible connection joint 299 allows for the support frame 218 and the valve frame 214 to travel between the collapsed state, as shown generally in FIG. 3, and the expanded state, as shown generally in FIGS. 1, 2, and 4, along a second travel path 206.

In one embodiment, the flexible connection joint 299 can include the portion of the first elliptical member 234 and the second elliptical member 238 at which the curve 274 occurs. FIG. 4 shows an additional embodiment of the flexible connection joint 499 that includes an integrated spring 410 where the support frame 418 joins to the valve frame 414 on the axis 420. The integrated spring 410 can have a circular or an elliptical coil configuration.

The first elliptical member 234 and the second elliptical member 238 can include a variety of cross-sectional shapes and dimensions. For example, cross-sectional shapes for the first elliptical member 234 and the second elliptical member 238 can include, but are not limited to, circular, tubular, I-shaped, T-shaped, oval, and triangular. The first elliptical member 234 and the second elliptical member 238 can also have a single cross-sectional shape (e.g., all of the first and second elliptical members 234 and 238 have a circular cross-sectional shape). In an additional embodiment, the first elliptical member 234 and the second elliptical member 238 can have two or more cross-sectional shapes (e.g., a circular cross-sectional shape in the elastic region 290 and a different cross-sectional shape in other regions of members 234 and 238).

Valve frame 214 and support frame 218 can further include one or more contiguous members. For example, valve frame 214 and support frame 218 can be formed from a single contiguous member that forms both the first elliptical member 234 and the second elliptical member 238. The single contiguous member can be bent around an elongate tubular mandrel to form both the valve frame 214 and the support frame 218. The ends of the single contiguous member can then be welded, fused, crimped, or otherwise joined together to form the first elliptical member 234 and the second elliptical member 238. In an additional embodiment, the valve frame 214 and the support frame 218 of the valve can be derived (e.g., laser cut, water cut) from a single tubular segment. The first elliptical member 234 and the second elliptical member 238 can be heat set by a method as is typically known for the material which forms the members 234 and 238.

In an additional embodiment, the valve frame 214 and the support frame 218 can each be formed from separate contiguous members that are joined as described herein. For example, a first contiguous member can be used to form the first elliptical member 234 and a second contiguous member can be used to form the second elliptical member 238 that is joined to the first elliptical member 234. Methods of joining members 234 and 238 to form the valve frame 214 and the support frame 218 at the first region 242 and the second region 246 can include, but are not limited to, welding, gluing, fusing, and intertwining (e.g., coaxially intertwining the integrated springs of the valve frame 214 and the support frame 218) the members that form the valve frame 214 and the support frame 218.

The valve frame 214 and the support frame 218 can be formed from a biocompatible metal, metal alloy, polymeric material, or combinations thereof, which allow the valve frame 214 and support frame 218 to self-expand and to move radially between the collapsed and expanded state, as discussed herein. To accomplish this, the biocompatible metal, metal alloy, or polymeric material should exhibit a low elastic modulus and a high yield stress for large elastic strains that can recover from elastic deformations. Examples of suitable materials include, but are not limited to, medical grade stainless steel (e.g., 316L), titanium, tantalum, platinum alloys, niobium alloys, cobalt alloys, alginate, or combinations thereof. In an additional embodiment, the valve frame 214 and the support frame 218 may be formed from a shape-memory material. Examples of a suitable shape-memory material include, but are not limited to, alloys of nickel and titanium in specific proportions known in the art as nitinol. Other materials are also possible.

FIG. 4 further illustrates an embodiment in which the valve frame 414 and the support frame 418 further include one or more anchoring elements. For example, the one or more anchoring elements can include, but are not limited to, one or more barbs 417 projecting from either, or both, of the valve frame 414 and the support frame 418, as shown in FIG. 4.

The valve can further include one or more radiopaque markers (e.g., tabs, sleeves, welds). For example, one or more portions of the valve frame 414, the support frame 418 and/or the barbs 417 can be formed from a radiopaque material. Radiopaque markers can be attached to and/or coated onto one or more locations along the valve frame 414, the support frame 418 and/or the barbs 417. Examples of radiopaque materials include, but are not limited to, gold, tantalum, and platinum. The position of the one or more radiopaque markers can be selected so as to provide information on the position, location and orientation of the valve during its implantation.

The valve further includes valve leaflets 119 joined to valve frame 114. The valve leaflets 119 can deflect between a closed configuration (FIG. 1A) in which retrograde fluid flow through the valve 100 is restricted, and an open configuration (FIG. 1B) in which antegrade fluid flow through the valve 100 is permitted. In one embodiment, valve leaflets 119 of the valve are configured to open and close in response to the fluid motion and/or pressure differential across the valve leaflets 119.

Valve leaflets 119 include surfaces, as discussed herein, defining a reversibly sealable opening 101 for unidirectional flow of a liquid. Valve 100 shown in FIGS. 1A and 1B provide embodiments in which the surfaces defining the reversibly sealable opening 101 include a first leaflet 124 and a second leaflet 128 coupled to the valve frame 114 to provide a two-leaflet configuration (i.e., a bicuspid valve) for valve 100.

Although the embodiments illustrated in FIGS. 1A and 1B of the present invention show and describe a two-leaflet configuration for valve 100, designs employing a different number of valve leaflets (e.g., tricuspid valve) are possible.

The valve leaflets 119 can have a variety of sizes and shapes. For example, each of the valve leaflets 119 (e.g., first leaflet 124 and second leaflet 128) can have a similar size and shape. In addition, each of the valve leaflets 119 can include opposed first and second major surfaces 130 and 132, respectively. Each first major surface 130 of valve leaflets 119 can be oriented to face an upstream end 140 of valve 100. Each of the valve leaflets 119 can further provide sealing surfaces 141 and 144 formed by portions of the first and the second leaflets 124 and 128, respectively, where sealing surfaces 141 and 144 can engage to define the closed configuration (FIG. 1A) of valve 100. Sealing surfaces 141 and 144 of valve leaflets 119 can separate to provide for an open configuration (FIG. 1B) of valve 100. In an additional example, each of the valve leaflets 119 need not have valve leaflets 119 that are of a similar size and shape (i.e., the valve leaflets can have a different size and shape).

Valve frame 114 can include an open frame construction (i.e., valve frame 114 defines an opening) through which valve leaflets 119 can radially-collapse and radially-expand. The valve leaflets 119 can be provided over the open frame construction of the valve frame 114 to direct fluid flow through reversibly sealable opening 101 under specific fluid flow conditions. In one embodiment, the material of the valve leaflets 119 coupled to the valve frame 114 can be sufficiently thin and pliable so as to permit radially-collapsing of the valve leaflets 119 for delivery by catheter to a location within a body lumen.

In one embodiment, each of the valve leaflets 119 includes sufficient excess material spanning valve frame 114 such that fluid pressure (e.g., antegrade flow) acting on the first major surface 130 of the valve leaflets 119 forces the valve 100 into an open configuration (FIG. 1B). Valve leaflets 119 further include arcuate edges 151 and 152 that are positioned adjacent each other along a substantially catenary curve between the first region 142 and the second region 146 in the closed configuration (FIG. 1A) of valve 100. Similarly, arcuate edges 151 and 152 can define opening 101 when the valve 100 is in the open configuration (FIG. 1B).

In an additional embodiment, in the open configuration the sufficient excess material spanning the valve frame 114 can allow the first and second major surfaces 130 and 132 to take on a semi-tubular structure 159, as shown in FIG. 1B, when fluid pressure opens the valve 100. In an additional embodiment, arcuate edge 151 and 152 of valve 100 can open to approximately the full inner diameter of body lumen 111.

Each of the second major surfaces 132 of the valve leaflets 119 can further include a curve imparted thereto so as to provide the second major surface 132 with a concave structure 164. The concave structure 164 allows the valve leaflets 119 to better collect retrograde fluid flow to urge valve leaflets 119 towards the closed configuration. For example, as retrograde flow begins, the valve leaflets 119 respond by moving towards the center of valve 100. As the valve leaflets 119 approach the center of the device the sealing surfaces 141 and 144 make sufficient contact to effectively close valve 100 and restrict retrograde fluid flow.

In an additional embodiment, the valve leaflets 119 can include one or more support structures. For example, the valve leaflets 119 can include one or more support ribs having a predetermined shape. In one embodiment, the predetermined shape of the support ribs can include a curved bias so as to provide the valve leaflets 119 with a curved configuration. Support ribs can be constructed of a flexible material and have dimensions (e.g., thickness, width and length) and cross-sectional shape that allows the support ribs to be flexible when valve leaflets 119 are urged into an open position, and stiff when the valve leaflets 119 are urged into a closed position upon experiencing sufficient back flow pressure from the direction downstream from the valve. In an additional embodiment, support ribs can also be attached to valve frame 114 so as to impart a spring bias to the valve leaflets in either the open or the closed configuration.

The valve leaflets 119 can be constructed of a fluid-impermeable biocompatible material that can be either synthetic or biologic. Possible synthetic materials include, but are not limited to, expanded polytetrafluoroethylene (ePTFE), polytetrafluoroethylene (PTFE), polystyrene-polyisobutylene-polystyrene, polyurethane, segmented poly(carbonate-urethane), Dacron, polyethlylene (PE), polyethylene terephthalate (PET), silk, urethane, Rayon, Silicone, or the like. Possible biologic materials include, but are not limited to, autologous, allogeneic or xenograft material. These include explanted veins and decellularized basement membrane materials, such as small intestine submucosa (SIS) or umbilical vein.

Valve leaflets 119 can be coupled to the various embodiments of valve frame 114, as described herein, in any number of ways. For example, a variety of fasteners can be used to couple the material of the valve leaflets 119 to the valve frame 114. In one embodiment, the material of the valve leaflets 119 can be wrapped at least partially around the valve frame 114 and coupled using the fastener. Fasteners can include, but are not limited to, biocompatible staples, glues, and sutures. In an additional embodiment, valve leaflets 119 can be coupled to the various embodiments of valve frame 114 through the use of heat sealing, solvent bonding, adhesive bonding, or welding the valve leaflets 119 to either a portion of the valve leaflet 119 (i.e., itself) and/or the valve frame 114. Valve leaflets 119 can also be attached to valve frame 114 according to the methods described in U.S. Patent Application Publication US 2002/0178570 to Sogard et al., which is hereby incorporated by reference in its entirety.

The valve leaflets 119 may also be treated and/or coated with any number of surface or material treatments. For example, the valve leaflets 119, the valve frame 114, and/or the support frame 116 can be treated with a non-thrombogenic biocompatible material, as are known or will be known. In an additional example, the valve leaflets 119, the valve frame 114, and/or the support frame 116 can be treated with one or more biologically active compounds and/or materials that may promote and/or prevent endothelization of the valve leaflets 119. Similarly, each of the valve leaflets 119 may be seeded and covered with cultured tissue cells (e.g., endothelial cells) derived from either a donor or the host patient which are attached to the valve leaflets 119. The cultured tissue cells may be initially positioned to extend either partially or fully over the valve leaflets 119.

Examples of possible non-thrombogenic biocompatible material coatings include block copolymers comprising at least one A block and at least one B block. The A blocks can include soft elastomeric blocks, which are based upon one or more polyolefins, or other polymer with a glass transition temperature at or below room temperature. For example, the A blocks can be polyolefinic blocks having alternating quaternary and secondary carbons of the general formulation: —(CRR'—CH$_2$)$_n$—, where R and R' are, independently, linear or branched aliphatic groups such as methyl, ethyl, propyl, isopropyl, butyl, isobutyl and so forth, or represent cyclic aliphatic groups such as cyclohexane, cyclopentane, and the like, either with or without pendant groups. Examples of polyolefinic blocks include polymeric blocks of isobutylene H$_2$C=C(CH$_3$)$_2$, (i.e., where R and R' are methyl groups). Other examples of A blocks include silicone rubber blocks and acrylate rubber blocks.

The B blocks can include hard thermoplastic blocks with glass transition temperatures significantly higher than the elastomeric A blocks which, when combined with the soft A blocks, are capable of, beside other things, altering or adjusting the hardness of the resulting copolymer to achieve a desired combination of qualities. Examples of B blocks include polymers of methacrylates or polymers of vinyl aromatics. More specific examples of B blocks include blocks that can be formed from monomers of styrene, styrene derivatives (e.g., α-methylstyrene, ring-alkylated styrenes or ring-halogenated styrenes or other substituted styrenes where one or more substituents are present on the aromatic ring) or mixtures of the same, collectively referred to herein as "styrenic blocks" or "polystyrenic blocks", or can be formed from monomers of methylmethacrylate, ethylmethacrylate, hydroxyethyl methacrylate or mixtures of the same.

The block copolymers are provided in a variety of architectures, including cyclic, linear, and branched architectures. Branched architectures include star-shaped architectures (e.g., architectures in which three or more chains emanate from a single region), comb architectures (e.g., copolymers having a main chain and a plurality of side chains), and dendritic architectures (including arborescent or hyperbranched copolymers).

Some examples of such block copolymers include, but are not limited to, the following: (a) BA (linear diblock), (b) BAB or ABA (linear triblock), (c) B(AB)$_n$ or A(BA)$_n$ (linear alternating block), or (d) X-(AB)$_n$ or X—(BA)$_n$ (includes diblock, triblock and other radial block copolymers), where n is a positive whole number and X is a starting seed, or initiator, molecule. One specific group of polymers have X-(AB)$_n$ structures, which are frequently referred to as diblock copolymers and triblock copolymers where n=1 and n=2, respectively (this terminology disregards the presence of the starting seed molecule, for example, treating A-X-A as a single A block, with the triblock therefore denoted as BAB). One example of a polymer from this group includes polystyrene-polyisobutylene-polystyrene triblock copolymer (SIBS). Where n=3 or more, these structures are commonly referred to as star-shaped block copolymers. Other examples of block polymers include branched block copolymers such as dendritic block copolymers, wherein at least one of the A and B blocks is branched, for instance, where the A blocks are branched and are capped by the B blocks.

Figure 6:
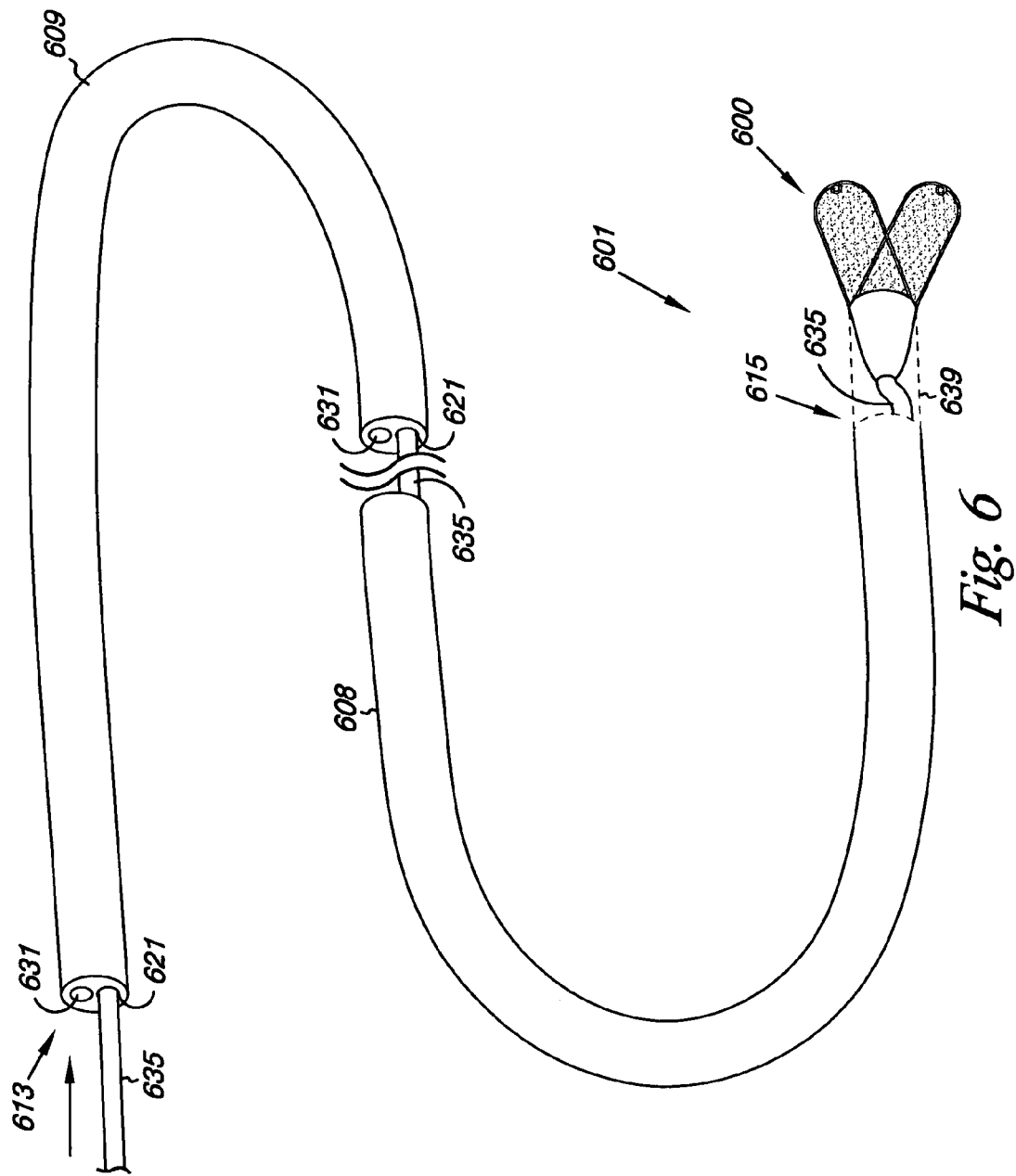
FIG. 6 illustrates an embodiment of a system that includes a valve.

FIG. 6 illustrates one embodiment of a system 601. System 601 includes at least one of the valves, as described herein, and a catheter 608. The catheter 608 includes an elongate body 609 having a proximal end 613 and a distal end 615, where a valve 600 can be located between the proximal end 613 and distal end 615. The catheter 608 can further include a lumen 621 longitudinally extending to the distal end 615. In one embodiment, lumen 621 extends between proximal end 613 and distal end 615 of catheter 608. The catheter 608 can further include a guidewire lumen 631 that extends within the elongate body 609, were the guidewire lumen 631 can receive a guidewire for positioning the catheter 608 and the valve 600 within a body lumen (e.g., a vein of a patient).

The system 601 can further include a deployment shaft 635 positioned within lumen 621, and a sheath 639 positioned adjacent the distal end 615. In one embodiment, the valve 600 can be positioned at least partially within the sheath 639 and adjacent the deployment shaft 635. The deployment shaft 635 can be moved within the lumen 621 to deploy valve 600. For example, deployment shaft 635 can be used to push valve 600 from sheath 639 in deploying valve 600.

Figure 7:
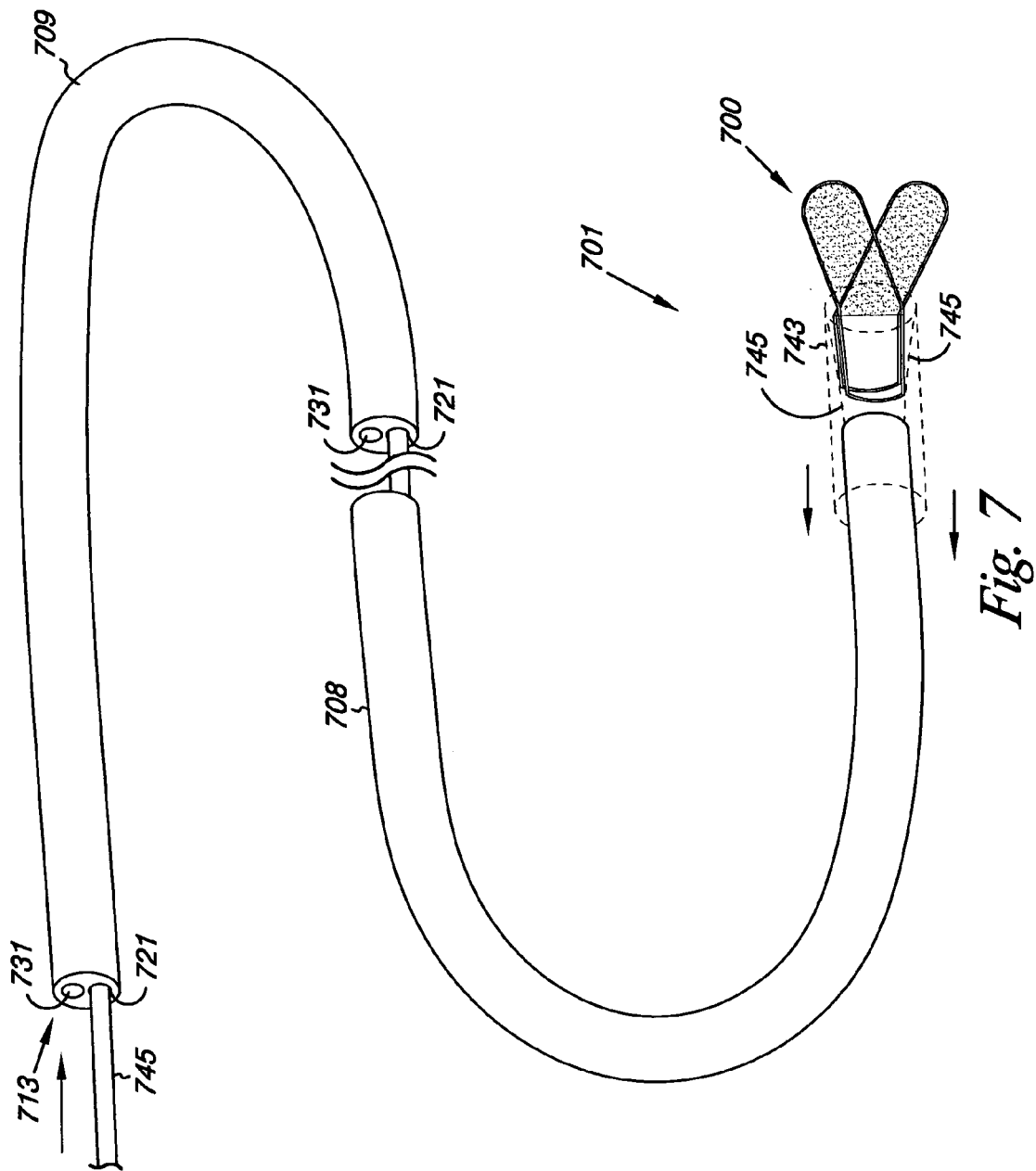
FIG. 7 illustrates an embodiment of a system that includes a valve.

FIG. 7 illustrates an additional embodiment of the system 701. The catheter 708 includes elongate body 709, lumen 721, a retraction system 745 and a retractable sheath 743. The retractable sheath 743 can be positioned over at least a portion of the elongate body 709, where the retractable sheath 743 can move longitudinally along the elongate body 709. The valve 700 can be positioned at least partially within the retractable sheath 743, where the retractable sheath 743 moves along the elongate body 709 to deploy the valve 700. In one embodiment, retraction system 745 includes one or more wires coupled to the retractable sheath 743, where the wires are positioned at least partially within and extend through lumen 721 in the elongate body 709. Wires of the retraction system 745 can then be used to retract the retractable sheath 743 in deploying valve 700.

Embodiments of the present invention can further include methods of forming the valve of the present invention. For example, the methods can include forming a valve, as discussed herein. Valve can include the valve frame, the valve leaflets joined to the valve frame, where the valve leaflets includes surfaces defining a reversibly sealable opening for unidirectional flow of a liquid. Valve can further include the support frame that meets the valve frame on an axis from which the valve frame and the support frame extend in an opposing direction.

Valve can then be reversibly joined to the catheter. Reversibly joining valve to the catheter can include altering the shape of valve from a first shape, for example an expanded state, to join valve and the catheter. For example, in reversibly joining valve and the catheter, the shape of valve can be altered into the compressed state. Valve can be reversibly joined with the catheter by positioning valve in the compressed state at least partially within the sheath of the catheter.

In one embodiment, positioning valve at least partially within the sheath of the catheter includes positioning valve in the compressed state adjacent the deployment shaft of the catheter. In an another embodiment, the sheath of the catheter functions as a retractable sheath, where valve in the compressed state can be reversibly joined with the catheter by positioning valve at least partially within the reversible sheath of the catheter.

Embodiments of the present invention can also include positioning and deploying the valve of the present invention. For example, at least part of a catheter that includes valve can be positioned at a predetermined location. In one embodiment, the predetermined location can include a position within a body lumen of a venous system of a patient. For example, positioning at least part of the catheter at the predetermined location includes positioning at least part of the catheter within a vein of a leg.

In one embodiment, positioning the catheter that includes valve within the body lumen of a venous system includes introducing the catheter into the venous system of the patient using minimally invasive percutaneous, transluminal catheter based delivery system. For example, a guidewire can be positioned within a body lumen of a patient that includes the predetermined location. The catheter, including valve can be positioned over the guidewire and the catheter advanced so as to position the valve at or adjacent the predetermined location. In one embodiment, radiopaque markers on the catheter and/or the valve can be used to help locate and position the valve.

The valve can be deployed from the catheter at the predetermined location. In one embodiment, valve of the present invention can be deployed and placed in any number of vascular locations. For example, valve can be deployed and placed within a major vein of a patient's leg. In one embodiment, major veins include, but are not limited to, those of the peripheral venous system. Examples of veins in the peripheral venous system include, but are not limited to, the superficial veins such as the short saphenous vein and the greater saphenous vein, and the veins of the deep venous system, such as the popliteal vein and the femoral vein.

As discussed herein, the valve can be deployed from the catheter in any number of ways. For example, the catheter can include a retractable sheath in which valve can be at least partially housed. Valve can be deployed by retracting the retractable sheath of the catheter, where the valve self-expands to be positioned at the predetermined location. In an additional example, the catheter can include a deployment shaft and sheath in which valve can be at least partially housed adjacent the deployment shaft. Valve can be deployed by moving the deployment shaft through the catheter to deploy valve from the sheath, where the valve self-expands to be positioned at the predetermined location.

In one embodiment, valve can provide sufficient contact and expansion force against the body lumen wall to prevent retrograde flow between the valve and the body lumen wall. For example, the valve can be selected to have a larger expansion diameter than the diameter of the inner wall of the body lumen. This can then allow valve to exert a force on the body lumen wall and accommodate changes in the body lumen diameter, while maintaining the proper placement of valve. As described herein, the valve can engage the lumen so as to reduce the volume of retrograde flow through and around valve. It is, however, understood that some leaking or fluid flow may occur between the valve and the body lumen and/or through valve leaflets.

In addition, the use of both the valve frame and the support frame of valve can provide a self centering aspect to valve within a body lumen. In one embodiment, the self centering aspect resulting from the support frame, in conjunction with valve frame, may allow valve to maintain a substantially coaxial alignment with the body lumen (e.g., such as a vein) as valve leaflets deflect between the open and closed configurations so as to better seal reversible opening when valve is closed.

While the present invention has been shown and described in detail above, it will be clear to the person skilled in the art that changes and modifications may be made without departing from the spirit and scope of the invention. As such, that which is set forth in the foregoing description and accompanying drawings is offered by way of illustration only and not as a limitation. The actual scope of the invention is intended to be defined by the following claims, along with the full range of equivalents to which such claims are entitled.

In addition, one of ordinary skill in the art will appreciate upon reading and understanding this disclosure that other variations for the invention described herein can be included within the scope of the present invention.

In the foregoing Detailed Description, various features are grouped together in several embodiments for the purpose of streamlining the disclosure. This method of disclosure is not to be interpreted as reflecting an intention that the embodiments of the invention require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A method, comprising:
   forming a valve that includes:
   a valve frame;
   a valve leaflet joined to the valve frame, wherein the valve leaflet includes surfaces defining a reversibly sealable opening extending between a first region and a second region for unidirectional flow of a liquid; and
   a support frame, where the support frame meets the valve frame at the first region and the second region on an axis that extends parallel with the reversibly sealable opening of the valve leaflet, and where the valve frame and the support frame extend from the axis in an opposing direction; and
   reversibly joining the valve and a catheter.

2. The method of claim 1, wherein the valve includes a first shape, and wherein reversibly joining the valve and the catheter includes altering the first shape of the valve to join the valve and the catheter.

3. The method of claim 1, wherein reversibly joining the valve and the catheter includes positioning the valve at least partially within a sheath of the catheter.

4. The method of claim 3, wherein positioning the valve at least partially within a sheath of the catheter include positioning the valve adjacent a deployment shaft of the catheter.

5. The method of claim 3, wherein the sheath includes a retractable sheath of the catheter.

6. The method of claim 1, wherein the valve frame and the support frame include a first elliptical member and a second elliptical member that meet at the first region and the second region opposite the first region on the axis.

7. The method of claim 6, wherein each of the first elliptical member and the second elliptical member include both a valve portion extending from the first region and the second region to form the valve frame, and a support portion extending from the first region and the second region in the opposing direction to form the support frame.

8. The method of claim 6, wherein the first elliptical member forms the valve frame and the second elliptical member forms the support frame.

9. The method of claim 1, wherein the valve leaflet includes a first leaflet and a second leaflet attached to the valve frame, the first leaflet and the second leaflet including a surface with a tubular structure when fluid opens the reversibly sealable opening and a concave structure when fluid closes the reversibly sealable opening.

10. A method, comprising:
    positioning at least part of a catheter including a valve at a predetermined location, wherein the valve includes:
    a valve frame;
    a valve leaflet joined to the valve frame, wherein the valve leaflet includes surfaces defining a reversibly sealable opening extending between a first region and a second region for unidirectional flow of a liquid; and
    a support frame, where the support frame meets the valve frame at the first region and the second region on an axis that is coextensive with the reversibly sealable opening of the valve leaflet, and where the valve frame and the support frame extend from the axis in an opposing direction; and
    deploying the valve from the catheter at the predetermined location.

11. The method of claim 10, wherein positioning at least part of the catheter at the predetermined location includes positioning at least part of the catheter within a vein of a leg.

12. The method of claim 10, wherein the catheter includes a retractable sheath, the valve at least partially housed within the retractable sheath, and deploying the valve from the catheter at the predetermined location includes retracting the retractable sheath of the catheter.

13. The method of claim 10, wherein the catheter includes a deployment shaft and a sheath, the valve at least partially housed within the sheath adjacent the deployment shaft, and deploying the valve from the catheter at the predetermined location includes moving the deployment shaft to deploy the valve from the sheath of the catheter.

14. The method of claim 10, wherein the valve frame and the support frame include a first elliptical member and a second elliptical member that meet at the first region and the second region opposite the first region on the axis.

15. The method of claim 14, wherein each of the first elliptical member and the second elliptical member include both a valve portion extending from the first region and the second region to form the valve frame, and a support portion extending from the first region and the second region in the opposing direction to form the support frame.

16. The method of claim 14, wherein the first elliptical member forms the valve frame and the second elliptical member forms the support frame.

17. The method of claim 10, wherein the valve leaflet includes a first leaflet and a second leaflet attached to the valve frame, the first leaflet and the second leaflet including a surface with a tubular structure when fluid opens the reversibly sealable opening and a concave structure when fluid closes the reversibly sealable opening.

* * * * *